US008099163B2

(12) United States Patent
Jung et al.

(10) Patent No.: US 8,099,163 B2
(45) Date of Patent: Jan. 17, 2012

(54) AUTOMATED DEFIBRILLATOR

(75) Inventors: Edward K. Y. Jung, Bellevue, WA (US);
Eric C. Leuthardt, St. Louis, MO (US);
Royce A. Levien, Lexington, MA (US);
Robert W. Lord, Seattle, WA (US);
Mark A. Malamud, Seattle, WA (US);
John D. Rinaldo, Jr., Bellevue, WA
(US); Lowell L. Wood, Jr., Livermore,
CA (US)

(73) Assignee: The Invention Science Fund I, LLC

( * ) Notice: Subject to any disclaimer, the term of this patent is extended or adjusted under 35 U.S.C. 154(b) by 877 days.

(21) Appl. No.: 11/397,354

(22) Filed: Apr. 4, 2006

(65) Prior Publication Data

US 2007/0233197 A1 Oct. 4, 2007

(51) Int. Cl.
*A61N 1/18* (2006.01)
*A61N 1/39* (2006.01)

(52) U.S. Cl. ................................. 607/5; 607/2
(58) Field of Classification Search .................. 607/5, 2; 606/1; 280/6.16
See application file for complete search history.

(56) References Cited

U.S. PATENT DOCUMENTS

| | | | |
|---|---|---|---|
| 3,942,536 A | 3/1976 | Mirowski et al. | |
| 4,928,690 A | 5/1990 | Heilman et al. | |
| 5,078,134 A | 1/1992 | Heilman et al. | |
| 5,090,464 A * | 2/1992 | Kauzlarich et al. | 152/310 |
| 5,211,213 A * | 5/1993 | Hicks | 152/323 |
| 5,649,718 A * | 7/1997 | Groglio | 280/641 |
| 6,427,083 B1 | 7/2002 | Owen et al. | |
| 6,827,364 B1 * | 12/2004 | Martin | 280/641 |
| 6,907,285 B2 | 6/2005 | Denker et al. | |
| 6,966,574 B1 * | 11/2005 | Dahl | 280/651 |
| 6,993,386 B2 | 1/2006 | Lin et al. | |
| 2002/0042630 A1 * | 4/2002 | Bardy et al. | 607/5 |
| 2002/0107546 A1 * | 8/2002 | Ostroff et al. | 607/5 |
| 2002/0120254 A1 * | 8/2002 | Julian et al. | 606/1 |
| 2003/0195567 A1 * | 10/2003 | Jayne et al. | 607/5 |
| 2004/0138713 A1 * | 7/2004 | Stickney et al. | 607/5 |
| 2004/0254566 A1 * | 12/2004 | Plicchi et al. | 606/1 |
| 2005/0189528 A1 * | 9/2005 | Rincoe | 254/424 |
| 2006/0087746 A1 * | 4/2006 | Lipow | 359/689 |

OTHER PUBLICATIONS

American Heart Association; "AED Programs Q & A"; Americanheart.org; bearing dates of Mar. 21, 2006 and 2005; printed on Mar. 21, 2006; pp. 1-3; at http://www.americanheart.org/presenter.jhtml?identifier=3011859.
American Red Cross of Central Maryland; "Automated External Defibrillators Save Lives!"; Redcross-cmd.org; printed on Mar. 21, 2006; pp. 1; at http://www.redcross-cmd.org/Chapter/Courses/aeds.html.

(Continued)

*Primary Examiner* — Carl H Layno
*Assistant Examiner* — Allen Porter, Jr.

(57) ABSTRACT

One aspect relates to defibrillating an individual potentially in an absence of any human assistance including that from the individual. Another aspect relates to positioning an electrode in electrical proximity to an individual when the individual is in an unusual defibrillating position; and applying a defibrillating charge to the individual at least partially via the electrode when the individual is in the unusual defibrillating position. Yet another aspect relates to securing at least one defibrillating electrode outside of a material associated with an individual relative to the individual; and extending at least one extensible electric contact(s) from the at least one defibrillating electrode through the material into an electric contact with at least a portion of the individual.

6 Claims, 11 Drawing Sheets

OTHER PUBLICATIONS

Bocka, MD, Joseph; "Automatic External Defibrillation"; Emedicine.com; bearing dates of Sep. 12, 2004 and 1996-2006; printed on Mar. 21, 2006; pp. 1-8; at http://www.emedicine.com/emerg/topic698.htm.

Medtronic; "Lifepak® 500 Automated External Defibrillator, Designed to be used by first responders to cardiac emergencies"; Medtronicphysiocontrol.com; bearing a date of 2006; printed on Mar. 21, 2006; pp. 1-2; at http://www.medtronicphysiocontrol.com/products/LP500.cfm.

Philips; "HeartStart OnSite Ddefibrillator, Owner's Manual, Guide to Set-Up, Operation, Maintenance, and Accessories"; bearing dates of Jan. 2005 and 2005; pp. 1-68; Edition 5; Philips Electronics North America Corp.

U.S. Department of Homeland Security; "Automatic External Defibrillator (AED) Use in the Coast Guard Alcoast 484/00"; printed on Mar. 21, 2006; pp. 1-2; at http://www.cgaux.info/g_pcx/publications/alcoast/alcoast-484-00.html.

Wikipedia; "Automated external defibrillator"; En.wikipedia.org; bearing a date of Mar. 17, 2006; printed on Mar. 21, 2006; pp. 1-3; at http://en.wikipedia.org/wiki/Automated_external_defibrillator.

Wisegeek; "What is a defibrillator?"; Wisegeek.com; bearing a date of 2006; printed on Mar. 21, 2006; pp. 1-2; at http://www.wisegeek.com/what-is-a-defibrillator.htm.

* cited by examiner

FIG. 7c wherein the individual includes a person 2006 wherein the individual includes an animal 2008

2000

| 7a | 7b |
| 7c | |

Key To FIG. 7

FIG. 8 positioning an electrode in electrical proximity to an individual when the individual is in an unusual defibrillating position 2202 extending at least a portion of the electrode through a clothing of the individual 2210 applying a defibrillating charge to the individual at least partially via the electrode when the individual is in the unusual defibrillating position 2204 displacing the individual into a usual defibrillating position 2212

2200

AUTOMATED DEFIBRILLATOR

TECHNICAL FIELD

Certain aspects, of this disclosure relates to, but is not limited to, defibrillation. Certain aspects, of this disclosure relate to sensing or monitoring a medical condition that may involve applying defibrillation. In addition, further aspects, embodiments, and features will become apparent by reference to the drawings and the following detailed description.

BRIEF DESCRIPTION OF THE FIGURES

FIG. 7, which includes FIGS. 7a, 7b, and 7c, is one embodiment of a flow chart as could be performed by one embodiment of the defibrillator;

FIG. 8 is one embodiment of a flow chart of an operation as could be performed by one embodiment of the defibrillator;

DETAILED DESCRIPTION

Figure 1:
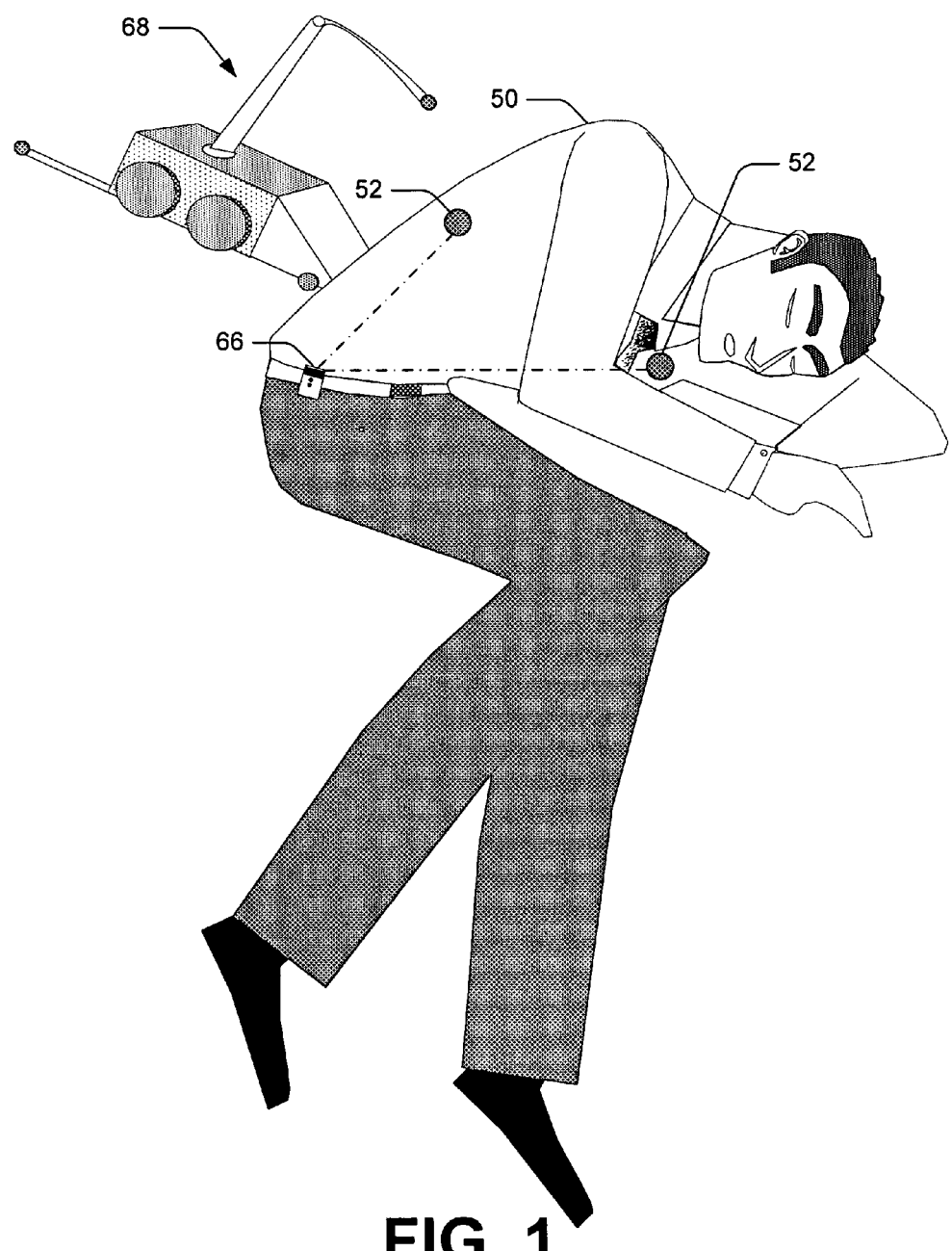
FIG. 1 is a block diagram of one embodiment of an individual in the proximity of a number of embodiments of a defibrillator.
Figure 2:
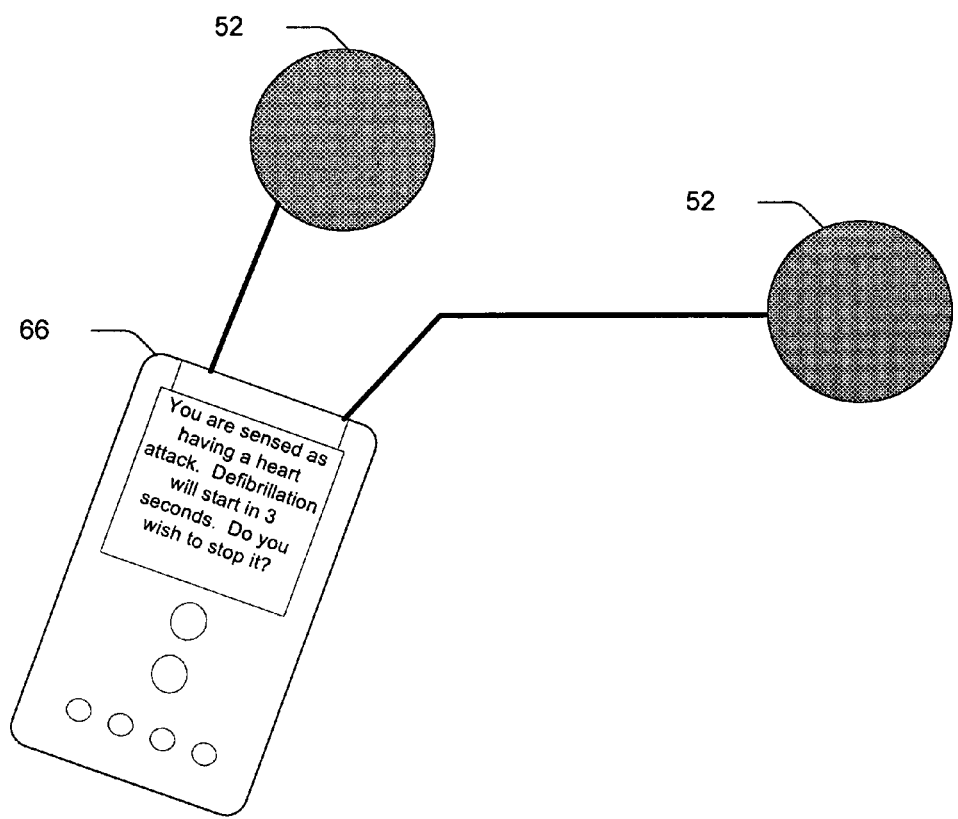
FIG. 2 is a diagram of one embodiment of a personal defibrillator, similar to as illustrated with respect to FIG. 1.

At least certain portions of the text (e.g., claims and/or detailed description) and/or drawings as set forth herein can support various different applications. Although, for sake of convenience and understanding, the detailed description includes section headings that generally track the titles of the various different supported applications, it is to be understood that support for the various applications appears throughout the text and/or drawings, irrespective of the section headings.

I. Certain Embodiments of Defibrillator

Certain aspects of this disclosure can relate to defibrillators. Certain aspects of this disclosure can also relate to defibrillator charges and operation. Certain aspects of this disclosure can also relate to electrodes as used by defibrillators. Defibrillators, in general, can apply a defibrillating charge to an individual 50 (e.g., a person or animal at a suitable location) in an attempt to return a condition of their heart and/or circulatory system to normal. During a heart attack, a fibrillation, an irregular heartbeat, and/or other serious heart-related medical conditions, it may be very desirable to be able to apply defibrillation to the individual 50 as quickly as possible. Within this disclosure, the term "individual" can, depending on context, describe an individual or animal who is being considered for defibrillation. Typically, time is of the essence for the individual 50 when the individual 50 is in need of defibrillation. Excessive additional time to apply the defibrillator and/or defibrillation can result in death, or diminished quality of life, incapacitation, etc. for the individual 50. As such, in many instances, an important issue in applying defibrillation is how quickly the defibrillation can be applied and/or performed. As such, it is important that defibrillation techniques and/or systems can be applied to the individual 50 properly, quickly, and/or reliably.

Within this disclosure, the term "individual" 50 may be used instead of the term "patient", primarily to indicate the desire to maintain the individual 50 in as close to a normal lifestyle as practicable during and/or following the defibrillation. It may be desired for many embodiments of the defibrillator, as described in this disclosure, to be capable of reviving the individual 50 in returning the individual to a useful life. In certain instances, the individual 50 may not even have to visit a hospital or doctor following their revival. Certain human individuals that have been revived 50 may select to pursue medical care, or hospitalization while others may not, depending upon such factors as the degree of the heart condition, the condition of the individual, etc.

Certain aspects or conditions of defibrillation can involve, but are not limited to, getting the heart (which is a muscle) to resume regular operation in a regular and efficient manner. In certain instances when the heart is not properly operating as in the case of a fibrillation and/or a heart attack, then the blood flowing through the body may not be flowing in an efficient manner. As such, problems or irregularities of the heart may also affect the circulating system such as by limiting the blood flow to or within the circulatory system. By defibrillating the individual 50, hopefully the effectiveness of the heart will return, and the blood flow, heart rate, muscle activity of the heart, and/or other heart or circulatory system condition, will hopefully return to normal for the individual. After the defibrillation, it may be important for certain embodiments of the defibrillator to evaluate whether the defibrillation has been successful; and if not successful then further defibrillating activities may be considered and/or provided. Suitable further activities can be programmed and/or pre-programmed into certain embodiments of the defibrillator, as described in this disclosure.

As described in this disclosure, certain embodiments of the defibrillator can sense a variety of conditions of the individual 50 that may involve the use of the defibrillator. For instance, the individual 50 may collapse as illustrated with respect to FIG. 1, which could be sensed using an inertial sensor or other sensor, for example; the blood flow or pressure of the individual 50 may be altered to indicate that the blood is not flowing through the body as it should be; an irregular heartbeat may be sensed; etc. It is well understood under which conditions each of the distinct types of defibrillation should be applied, as well as the differing potential defibrillation techniques and mechanisms. As such, the conditions, techniques, and mechanisms that are associated with defibrillation will not be gone into considerable detail in this disclosure. There are a variety of operations that can be performed by certain embodiments of the defibrillator that can include defibrillation, monitoring, sensing, and/or providing pacemaking, etc. as described in this disclosure.

There can be a variety of sensors or monitors (not shown) that can sense the individual for a fibrillating condition. For instance, a blood pressure sensor device, a blood flow sensor device, a heart rate sensor device, a heart blood-volume pumped sensor device, and/or another suitable sensor device could be used as the sensor or monitor of the fibrillating condition under which conditions defibrillation can be applied. Certain embodiments of the sensors or monitors can be electric-based, electronic-based, optical-based, electromagnetic-based, and/or can utilize a variety of other suitable, combined, or modified technologies. Certain embodiments of the sensors can be general-purpose devices and/or specific-purpose devices, and can rely upon hardware aspects, software aspects, firmware aspects, mechanical aspects, electro-mechanical aspects, and/or a combination of these aspects. Such sensors can rely upon microprocessor-technology, computer-technology, controller-technology, mote-technology, and/or a combination of these, etc. Certain embodiments of motes, for example, are relatively small solid-state wireless sensor, communication, and/or controller devices that can be implanted or distributed at a desirable location or environment (and configured to operate to sense or monitor to hopefully detect a fibrillating condition). For example, one or more motes could be applied to the heart, the aorta, or another suitable location of the individual. Certain embodiments of the mote could thereupon be configured to continuously sense for a fibrillating condition, and only be actuated to transmit a suitable signal to the defibrillator upon sensing the fibrillating condition. Upon an indication of the fibrillating condition, the sensor or monitor (e.g., mote), could thereupon transmit suitable fibrillating information to the defibrillator. Thereupon, certain embodiments of the defibrillator as described in this disclosure (e.g., with respect to FIGS. 1 to 6, etc) could be actuated to defibrillate the individual.

Since certain embodiments of the defibrillator can sense a variety of irregular heart conditions, heart attacks, fibrillating conditions, etc., it may be envisioned that certain embodiments of the defibrillator can be associated with the individual 50 for an extended period. For example, certain individuals 50 who suspect (or whose doctors or medical advisors suspect) they might experience irregular heart conditions, or have a history thereof, may use certain embodiments of the defibrillator through the day and/or night to reduce the probability of fibrillation conditions. Certain embodiments of clothes, sleepwear, exercise wear, harnesses, belts, undergarments, etc. can be configured to either integrate at least a portion of the defibrillator (e.g., the defibrillator and/or the electrodes as described in this disclosure), or alternately at least certain ones of the portions of the defibrillator may be integrated relative to the clothing or within the clothing after manufacture. In addition, certain embodiments of beds, furniture, etc. can be provided with one or more of the defibrillators as described in this disclosure. As such, individuals could be provided with access to relatively reliable, safe, and cost-effective defibrillation on a substantially continuous basis while being allowed to live as normal of a life as practicable.

Certain embodiments of the at least one electrode(s) 52 that can be utilized with certain embodiments of the defibrillator, as described in this disclosure, can during operation (e.g., during defibrillation) extend through clothing or other material. For example, if it is determined that the individual 50 is in a condition in which defibrillation should be applied, certain embodiments of the at least one electrode(s) 52 can be extended through clothing, etc. to provide an electrical contact of the at least one electrode with at least a portion of the individual (such as the individual's skin).

Certain embodiments of the at least one electrode(s) 52 may be positioned relative to the individual's skin in a similar manner to traditional defibrillators. Certain embodiments of the at least one electrode(s) can be configured, sized, or operated in a manner suitable for the particular defibrillator and/or the defibrillating charges as described in this disclosure. Other embodiments of the at least one electrode(s) 52 may be implanted within the patient, in a similar manner to an electrode for a pacemaker. As such, certain embodiments of a defibrillating charge can be applied to a precisely determined internal position based, at lest in part, on the internal location of the electrode.

It is therefore to be understood that the electrodes 52, and/or the techniques of applying the electrodes, can vary depending upon such factors as the individual's preference, the individual's condition, this general activity of the individual, the type of defibrillating charge that could be applied to the individual, etc. Certain embodiments of the electrodes 52, as described in this disclosure, are to be illustrative in nature and not limiting in scope.

By configuring certain embodiments of the defibrillator be configured to be able to sense the irregular heartbeats, heart attacks, fibrillating conditions, etc., certain embodiments of the defibrillator can be configured to apply defibrillation soon after the regular heartbeat, fibrillating conditions, etc. are sensed. As such, with many embodiments of traditional defibrillator systems and/or techniques, the application of the defibrillation charge may be delayed for a considerable period as necessary for trained medical personnel (or individuals 50 who know how to use traditional automated defibrillators) to arrive and apply the more traditional defibrillation techniques and/or systems. Certain embodiments of the defibrillator, as described in this disclosure, can be configured to sense the irregular heartbeats, fibrillating conditions, etc., and therefore can act relatively quickly and limit the duration of which the defibrillation is not being applied.

Certain aspects of this disclosure can relate to, but are not limited to, defibrillating the individual 50 who may be a person or animal. As used in this disclosure, the term "individual" 50 may thereby be intended, depending on context, to apply to animals (land and/or sea) as well as humans. Certain embodiments of the defibrillator could have to be modified depending on the type of the individual 50, as well as the size, condition, medical history, or other factors that may concern the defibrillation relative to the individual.

There may be a variety of situations in which the individual 50 in need of defibrillation may be alone and/or unreachable by others. For example, the individual 50 may work alone, live alone, be situated at some remote location, be traveling in their vehicle by themselves, etc. As such, it may be desired in many instances for the defibrillator to be able to apply the defibrillation techniques either with or without the assistance of the individual 50 (who may be unconscious or debilitated) and/or any other humans which there may not be at that particular time. Certain embodiments of the defibrillator, as described in this disclosure, can therefore be operable to be applied to the individual 50 potentially in the absence of, or remote from, other effective human assistance. In certain embodiments where defibrillation may be appropriate, the individual 50 may even be unconscious or severely incapacitated. Certain embodiments of the defibrillator can even be applied to unconscious patients even the absence of other human assistance.

Unconscious individuals 50 often may not fall or collapse in a manner that would allow application of many traditional defibrillation techniques and/or systems. The individual 50 may have to be in a prone position (lying on their back) or other "usual defibrillation positions" to receive defibrillation using many traditional defibrillators. Often, many traditional defibrillators require the removal of much of the clothing above the individual's 50 waist to apply defibrillation. There may be a number of defibrillation conditions under which it is undesirable to remove the patient clothing during defibrillation, either due to coldness, isolation, and/or privacy issues. Consider the number of skiers, mountain climbers, or scuba divers, or other individuals who are situated where undressing would be difficult and/or time consuming, for example; and may suffer from heart attacks, irregular heartbeats, or other fibrillating conditions. As such, the proper application of the defibrillation may be delayed for a considerable duration with certain traditional defibrillators during such activities. Such delay may represent a duration that may kill, incapacitate, or seriously injure certain ones of the individuals. Such delay may also represent a potential reduction in the quality of life for certain ones of the individuals. Additionally, such delay may represent considerable medical expenses for hospitals, doctors, and/or others associated with maintaining and/or treating the individuals.

While this disclosure describes certain embodiments of the defibrillator that can be utilized and/or operate in the absence of interaction with the individual 50, or alternately interaction with other assisting person(s), is to be emphasized that certain embodiments of the defibrillator can still be applied to unconscious individuals, medical personnel, and/or other assisting persons. As such, certain embodiments of the defibrillator (e.g., a personal defibrillator 66, or alternately an electric positioning defibrillator 68) as described in this disclosure could include user input (e.g., a graphical user interface) that could be utilized to actuate the defibrillator 66 or 68.

For instance, consider a situation in which the individual 50 is wearing the personal defibrillator 66 and/or the electrode positioning defibrillator 68 as described with respect to this disclosure, and the individual may lose consciousness or display some other conditions or symptoms at least partially as a result of a heart condition in the middle of an area where there are other people. Certain embodiments of the personal defibrillator and/or the electrode positioning defibrillator should be able to be activated either by itself (e.g., automatically), by the individual, and/or by people other than the individual upon the recognition of the condition. As such, while may be desirable to allow certain embodiments of the personal defibrillator 66 to defibrillate automatically, it is also important to allow the individual and/or other people (either medically trained or other) to operate the defibrillator. For example, if the individual is having a heart attack or other serious fibrillation condition, the personal defibrillator 66 should be able to both operate at least somewhat automatically as described in this disclosure and/or be actuated by the individual or other people in the vicinity to perform a suitable defibrillation.

Certain embodiments of the defibrillator that can operate at least somewhat-automatically upon sensing a fibrillating condition (e.g., a condition that can use defibrillation) may be configured to apply defibrillation as soon as at least one fibrillating condition is sensed. Certain embodiments of the defibrillator can operate with or without the need of medically trained personnel and/or other untrained people, such as might be used with traditional automated defibrillator systems. Since certain embodiments of the defibrillator as described in this disclosure can be applied relatively quickly, the amount of medical damage resulting from the heart attacks, fibrillating event, or irregular heartbeat can thereby be limited as compared to traditional defibrillators. By limiting the amount of medical damage resulting from the heart attacks, fibrillating events, and/or regular heartbeat, the number of the individuals 50 who have been defibrillated and are likely to require medical care, hospitalization, and/or die at least partially as a result of their subsequent heart condition should thereby be reduced. In addition, the medical condition of many of the individuals 50 undergoing defibrillation utilizing many embodiments of the defibrillator as described in this disclosure should be better than their condition had they undergone defibrillation using traditional defibrillators.

Certain embodiments of traditional automated defibrillators may be configurable to be applied by untrained medical personnel. A basic premise behind such traditional automated defibrillators is that even though the untrained medical personnel may apply the traditional automated defibrillators improperly, at least some improperly applied defibrillation may be equal to or better than no defibrillation at all. Such traditional automated defibrillators may often be available in offices, auditoriums, remote areas, vehicles, or other areas. Many embodiments of such traditional automated defibrillators are relatively expensive, and as such relatively few defibrillators may be spread over a large area. As such, access to many embodiments of such traditional automated defibrillators may be difficult and/or such defibrillators can be sparely situated. In general, the number of people who actually know how to quickly and effectively apply the traditional automated defibrillators may be relatively low, and many people who would consider applying such traditional automated defibrillators may feel some level of trepidation, confusion, and/or a general undesired, or lack of knowledge or ability, to apply such traditional automated defibrillators. After all, few untrained medical personnel could accurately determine which specific ones of the individual's 50 conditions merits defibrillation. Certain individuals may not desire to "get involved" in a defibrillation, even in a life or death situation. Additionally, there may be a number of reasons why it may be undesirable to take off at least some of someone else's or some of one's own clothing for defibrillation, especially in harsh or cold climates, and/or in the presence of certain other people.

Since human individuals come in different sizes, positions, weights, etc.; certain embodiments of the defibrillator can be configured to be applied to individuals 50 having different sizes, positions, weights, medical conditions, etc. In certain situations, when defibrillation is being applied, it should be ensured that the individual 50 does not end up in a worse condition following defibrillation than prior to defibrillation as a result of the defibrillation. Since defibrillation can typically be applied to critically ill individuals 50 whose condition may be most properly treated that do not result in initial subsequent revival, additional and/or alternate defibrillation techniques and/or systems may typically be provided with a considerable amount of leeway (medical, legal, or other) to revive the individual 50. As such, defibrillation may be allowed to be applied in a variety of situations and/or patient conditions since the alternative(s) may be so dire. Such leeway of the conditions or patients to which certain types of defibrillation may be applied may not be afforded by other non-defibrillating medical equipment that may be configured, for example, to maintain a non-critical patient.

As such, certain embodiments of the defibrillator can be utilized to physically reposition the patient in such a manner that defibrillation may be applied to the individual 50, or alternatively position the electrodes of the defibrillator relative to the patient. For instance, if the individual 50 is lying face down, in certain defibrillation application instances, the patient would have to be turned over to apply the defibrillation using certain traditional defibrillators. Certain embodiments of the defibrillator, as described in this disclosure by comparison, could subsequently to repositioning the individual apply defibrillation to individuals 50 who may be repositioned into the unusual defibrillation position, such as face down and/or on their side. In addition, certain embodiments of the defibrillator, as described in this disclosure, could apply defibrillation while maintaining the individual 50 clothed and/or comfortable.

Certain embodiments of the defibrillator can be applied to the individual 50 who might be suffering from a heart attack, fibrillation, irregular heartbeats, etc. FIG. 1 illustrates a medical situation in which the individual 50 has been overcome by a heart attack, a fibrillation, and/or irregular heartbeats, or the like. Within this disclosure, a defibrillator can apply defibrillation to the individual 50. Within this disclosure, two types of defibrillators are described with respect to FIG. 1 which may operate either together and/or separately. Certain operations as described in this disclosure may be performed by one or both of the defibrillators, as described with respect to FIG. 1.

Certain embodiments of the defibrillator, as described with respect to FIGS. 1, 2, 3, and 4 can, depending upon context, be referred to as a personal defibrillator 66. Certain embodiments of the personal defibrillator can include a capacitive element as described in this disclosure that can allow for the defibrillator to charge a sufficient voltage, current, and/or duration level, and thereupon discharge at a suitable voltage, current, and/or duration to provide the defibrillation. It is envisioned that certain embodiments of the personal defibrillator can be automatically actuated to defibrillate the individual 50 without assistance from the individual being defibrillated, or assistance from another person (medically trained or other). Certain portions of certain embodiments of the personal defibrillator 66 may, for example, fit in pockets of clothing for the individual 50, be integrated or sewn within an item of clothing to be worn by the individual 50, be integrated or sewn into a sleep garment or pajamas to be worn by the individual, be attached to a belt or belt loop of the individual, etc.

As such, certain embodiments of the personal defibrillator 66 may be configured to be maintained with the individual 50 on a substantially continuous basis, when the individual is asleep, or during some appropriate period. As described in this disclosure, certain embodiments of the components of the personal defibrillator 66 may be designed to be, and/or intended to be, relatively unobtrusive and/or comfortable to wear by the individual 50.

Another embodiment of the defibrillator as described in this disclosure is referred to as the electrode positioning defibrillator 68. Certain embodiments of the electrode positioning defibrillator can be operable to move the individual 50 from an unusual defibrillation position (in which the electrodes may not be applied to the individual) into an electrode-applying position (in which the electrodes may be applied to the individual). A variety of mechanisms can be utilized to move the individual 50 from the unusual defibrillation position into the electrode-applying position. Certain embodiments of the electrode positioning defibrillator can wedge and/or position the electrode relative to the individual. Typical embodiments of defibrillators can rely on a first electrode positioned outside the skin of the chest cavity proximate the heart, and another electrode positioned along the individual's 50 ribs or side (opposed to the ribs). In certain instances, therefore, at least one electrode might be positioned under the individual 50 who can be situated in an unusual defibrillation position such as lying on their stomach by the electrode positioning defibrillator.

The individual 50 as illustrated in FIG. 1, for example, can be considered to be in the unusual defibrillation position since the individual 50 might have to be repositioned to position an electrode on the heart of the individual using conventional electrodes. In certain embodiments, an unusual defibrillation position may be considered a position of the individual 50 in which the electrode positioning defibrillator 68 can not position electrodes in contact with the individual to apply the defibrillation. As such, certain embodiments of the electrode positioning defibrillator 68 can include an individual moving portion 70, which in certain embodiments can appear somewhat similar to a wedge that can be driven under the individual 50 to roll over, move, or otherwise reposition the individual. Other embodiments of the electrode positioning defibrillator can position and/or force at least one electrode with respect to the individual to allow positioning of the at least one electrode, and thereby provide defibrillation. Certain embodiments of the electrode positioning defibrillator 68 can also include a motive portion 72 that can provide sufficient force to move the individual 50 into a position to allow placement of the electrodes. Other embodiments of the motive portion 72 of the electrode positioning defibrillator can be sufficiently strong to drive the electrode under, around, or relative to the individual 50 as necessary to position the electrode when the individual is in an unusual defibrillation position.

Certain embodiments of the electrode positioning defibrillator 68, as described in this disclosure, can be configured to operate at least partially automatically; alternatively, certain embodiments of the electrode positioning defibrillator can operate to assist, or with the assistance of, the individual 50 and/or other people. For instance, certain embodiments of the electrode positioning defibrillator 68 can be configured to assist a person to apply electrodes to the individual when the person is incapable of positioning the electrodes themselves since, for example, the individual may be too large or in a precarious position for the person to turn over; the individual is in too precarious of a physical or medical condition to roll over, and/or it is desired to provide the defibrillation is some unusual defibrillation position, etc.

Certain embodiments of the personal defibrillator 66, as well as certain embodiments of the electric positioning defibrillator 68, can be configured to provide a variety of defibrillation techniques. One embodiment of a defibrillation technique may involve, for example, applying a sufficient defibrillating charge as to revive the patient. Certain embodiments of such defibrillating charge may involve a relatively high voltage coupled with a relatively low current. The electric voltage, current, and/or duration values of certain embodiments of the defibrillating charges as provided by traditional defibrillators are generally known, and will not be further described herein. Certain embodiments of the defibrillating charge may be similar to those utilized by the defibrillators in emergency rooms, as well as the automated defibrillators that may be applied by non-medial personal.

Another embodiment of the defibrillating technique may involve, for example, applying a sufficient pacemaking charge as to return the individual's heart beat, heart operation, and/or the heart rate back to some degree of normalcy for the individual. Certain embodiments of the pacemaking charge may be similar to those utilized by pacemakers as are commonly inserted into heart patients. A variety of defibrillating control systems and/or techniques can determine a suitable type of defibrillation, as well as the associated currents and/or voltage that may be appropriate to be applied across the electrodes of the defibrillator. The pacemaking charges and/or techniques are considered to be one embodiment of the defibrillation as described in this disclosure.

Certain embodiments of the defibrillating charge and/or the pacemaking charge (and the associated currents and/or voltages relating thereto), as described in this disclosure, are intended to be illustrative in nature but not limiting in scope. Other defibrillating techniques and/or systems from those described in this disclosure could be applied using certain embodiments of the defibrillator, while remaining within the scope of defibrillation as described in this disclosure. In addition, it is likely that the defibrillating and/or pacemaking techniques might be modified as the technologies evolve, and many of the concepts of the defibrillator as described in this disclosure could perform many of these modified or evolving techniques many of the concepts described in this disclosure are similarly modifiable.

II. Certain Embodiments of the Personal Defibrillator

Certain aspects of the personal defibrillator 66 are described with respect to FIGS. 1, 2, 3, 4, and/or at other locations in this disclosure. Certain embodiments of a generalized block diagram of the personal defibrillator 66 are described with respect to FIG. 3. One embodiment of a flow chart of a defibrillation process, as might be performed by certain embodiments of the personal defibrillator, are described with respect to FIG. 4. The embodiments of the personal defibrillator 66 as described with respect to FIGS. 1, 2, 3, 4, and/or at other locations in this disclosure are intended to be illustrative in nature and not limiting in scope. Certain embodiments of the personal defibrillator 66 may be configured to be able to provide a suitable defibrillation for the individual 50 who would benefit from the defibrillation. As mentioned elsewhere in this disclosure, defibrillation can be used to attempt to revive the individual 50 from a heart attack, an irregular heartbeat, etc.: or alternatively the defibrillation can be a pacemaking defibrillation, such as to produce or provide a regular heartbeat. In many instances, defibrillation may represent only a positive, since when, properly, successfully, and timely applied, the individual may likely fully recover. When the defibrillation is improperly applied, not applied at all, or unsuccessfully or untimely applied, the defibrillation may result in possible death, reduction in quality of life, personal capabilities, etc.

Certain embodiments of the personal defibrillator may be configured to be able to perform a variety of operations relative to defibrillation which can include, but are not limited to: a) sensing or monitoring whether the individual 50 is in need of the defibrillation, b) providing a defibrillating charge to the individual 50; c) at least partially control and/or monitor applying the defibrillating charge to the individual 50; and/or d) interfacing with a controller (or multiple controllers) to allow the distinct defibrillation controller to at least partially control and/or monitor applying the defibrillating charge to the individual 50.

Certain embodiments of the personal defibrillator 66 can include at least one electrode 52 (which are typically configured as a pair of electrodes including a first electrode and the second electrode). In certain instances during defibrillation, the first electrode can be applied to the proximate the heart of the individual 50, and the second electrode can be applied to a suitable remote area of the individual's 50 body, such as the skin area over the right rib cage. Certain embodiments of the electrode, as described in this disclosure, can be actuated with the individual 50 either in their usual defibrillation position such as on their back; or an unusual defibrillation position, such as face-down or on their side. Certain embodiments of the electrode, as also described in this disclosure, can be actuated with the individual 50 only in their usual defibrillation position.

Figure 3:
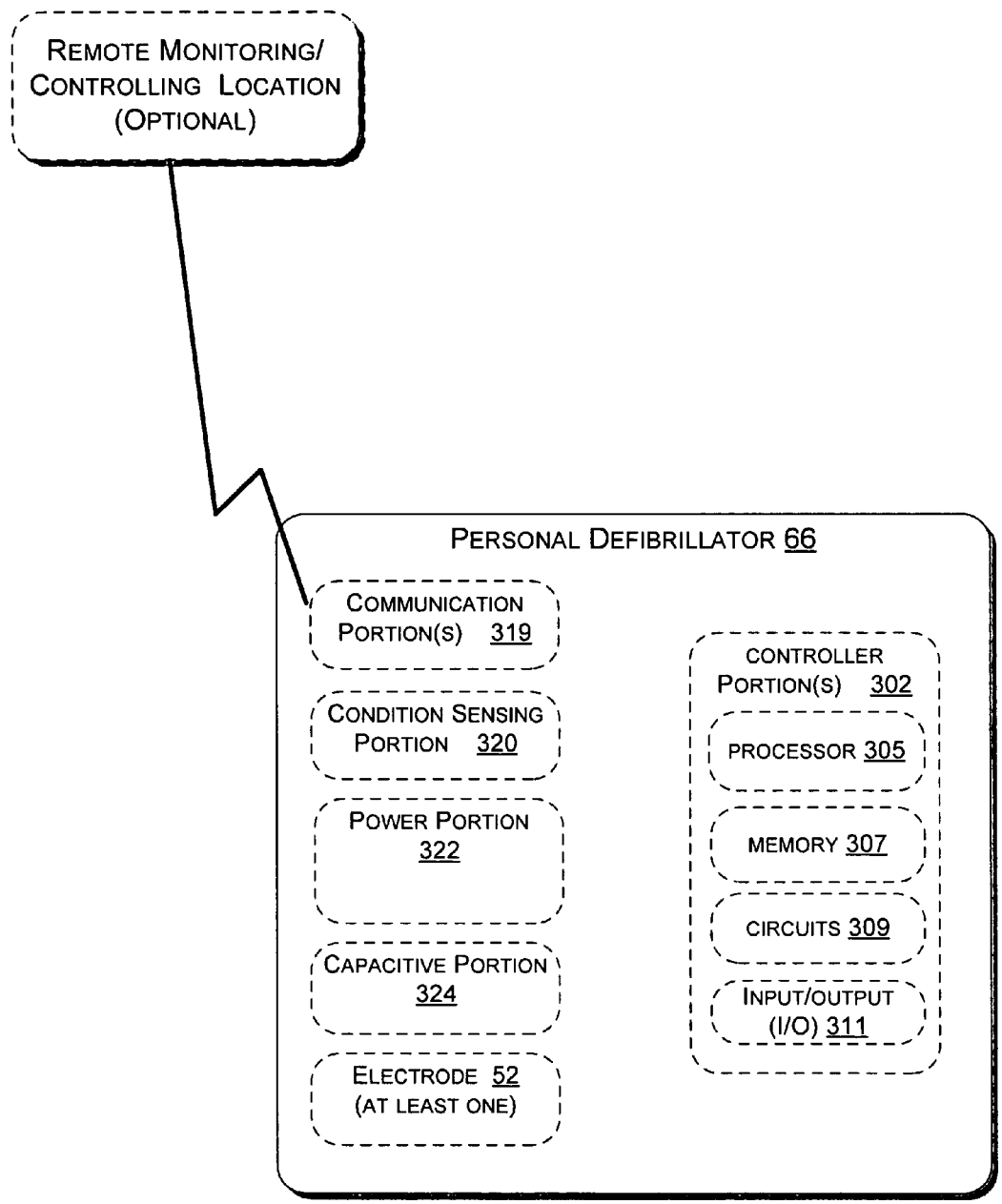
FIG. 3 is a block diagram of one embodiment of the personal defibrillator.

A more detailed description of certain aspects of the personal defibrillator 66 is now described with respect to FIG. 3. FIG. 3 shows another embodiment of the personal defibrillator 66 that can be computer based, controller based, mote based, and/or electronics based. As such, this disclosure describes a number of components of the personal defibrillator 66 that can operate utilizing computer-based technology to perform a variety of the maintaining, sensing, defibrillating, and other processes as described with respect to this disclosure. Certain embodiments of the flow charts of this disclosure can be effected by certain embodiments of the controller of certain embodiments of the personal defibrillator 66.

Certain embodiments of the personal defibrillator 66, as described with respect to FIG. 3, can include a variety of elements that can provide a variety of operations related to defibrillation. Certain embodiments of the elements can include, but are not limited to, a condition sensing portion 320, a power portion 322, the capacitive portion 324, the electrode 52, a communication portion 319, and/or a controller portion 302.

Certain embodiments of the condition sensing portion 320, as described with respect to FIG. 3, can determine whether the individual 50 is having a heart or circulatory condition that can utilize defibrillation. Examples of such heart or circulatory condition can include, but is not limited to, a heart attack, a heart rate irregularity, a heart fibrillation, a heart-pumping reduction, a fibrillation, and/or an other condition that indicate that the individual's heart is not operating as desired and should be revived. A variety of techniques may be utilized since the conditions at least partially utilizing the condition sensing portion 320 can include, but is not limited to, blood-pressure monitors or blood flow monitors (which may utilize acoustic, electronic, optical, electromagnetic, or other technology). Other techniques that can be used to assess whether the individual 50 should be defibrillated can include a consciousness indicator (e.g., the individual passes out in a manner attributable to heart and/or circulatory system problems), and individual response indicator, input of the individual or another person to indicate that the individual may be in need of defibrillation, etc. As such, other conditions from heart rate, blood pressure, etc. can also be used to determine that defibrillation should be applied.

Certain embodiments of the power portion 322 can be utilized to provide the power to the personal defibrillator 66, as well as the power associated with the defibrillating charge. In certain embodiments, the power portion 322 can include a battery or other electrical source that is sufficient to establish the defibrillating charge either directly and/or via the capacitor portion 324. The voltages and/or current associated with the defibrillating charge to vary depending upon the type of defibrillating charge. For example, defibrillating an individual to revive them from a heart attack irregular heartbeat, fibrillation, etc. might require a relatively high voltage, while defibrillating an individual to provide pacemaking might utilize a considerably lower voltage.

Certain embodiments of the personal defibrillator 66 can include the capacitor portion 324 that can allow the voltage level provided by the power portion 342 to be increased to a greater level than that could otherwise be provided by the power portion without the capacitor portion, and thereby affect a relatively high-voltage defibrillation. As such, for example, a relatively small power portion such as one or more batteries (such as one that can power consumer-electronics type device(s) can utilize and/or interface with the capacitor portion 324 to provide a sizable defibrillation charge. Certain embodiments of the defibrillation charge may be associated with a considerable voltage, as well as a relatively small current and duration for the defibrillating charge. As such, certain embodiments of the capacitor portion 324 can be configured to provide a suitable electrical voltage, current, and/or duration capability for the particular desired defibrillating charge. The particular type of defibrillating charge and its voltage, current, and/or duration can be controlled by a controller, such as a micro-processor based or electronics-based controller.

Certain embodiments of the at least one electrode 52, as described in this disclosure, can be configured to provide the appropriate defibrillating charge to the individual 50, as described in this disclosure. As such, certain embodiments of the electrode 52 can be positioned and/or taped (e.g., using medical tape) relative to the individual at an appropriate location. An example of an appropriate location may be one electrode taped or positioned next to the skin adjacent the individual's heart, and another electrode taped or positioned at some remote locations such as the individual's right rib.

Another embodiment of the at least one electrode 52, as described in this disclosure, can utilize an extending portion which, when actuated, may extend through at least some of the material of the patients clothing. In certain embodiments, the electrode 52 can be at least partially sewn into the clothing, undergarment, etc., while in other embodiments the electrode can be worn on a belt or heart is relative to the clothing. For instance, certain electrodes could be situated in such clothing as may be nearby a suitable location for an electrode, such as within or attached to a woman's bra. As such, a variety of permanence of the electrode 52 relative to the clothing can be provided, as desired or comfortable to the individual. As such, it may be desired to reduce any inconvenience or discomfort which may be provided to the individual by the defibrillator and/or the electrode 52. Certain embodiments of the electrode could be physically removed from the clothing, such as during washing, while other embodiments of the electrode could be washable.

Certain embodiments of the at least one electrode 52 can also be surgically applied to the individual 50, in similar manner to pacemakers. In certain embodiments, a utilizing the power portion 322 in combination with the capacitor portion 324 to provide potentially greater voltages as described in this disclosure, certain embodiments of pacemakers could also be adapted to defibrillate the individual, as described in this disclosure.

Certain embodiments of the personal defibrillator 66 can thereby also include the communication portion 319, which is configured to establish communications and/or transfer data to other computer and/or controller devices that may be associated with monitoring defibrillation conditions, sensing defibrillation conditions, controlling defibrillation, providing defibrillation, and/or other defibrillation-related activities. Such communication and/or data transfer of the personal defibrillator 66 utilizing the communication portion 319 that could be understood by those skilled in networking, computer, and/or controller techniques and/or technologies. Certain embodiments of the personal defibrillator 66 can operate as a stand-alone device, and thereby without the communication portion 319.

As described within this disclosure, multiple ones of the different embodiments of the personal defibrillator 66 can transfer information about the individual 50 or their condition, image information, data, signals, etc. via a communication link (typically using wireless technology) to or from the remote monitoring location 330 or some intermediate device. As such, certain embodiments of the personal defibrillator 66 can utilize networking processing, task-sharing, local sharing, and/or other computer-based techniques or mechanisms. One embodiment of the controller portion 302 can include a processor 305 such as a central processing unit (CPU), a memory 307, a circuit or circuit portion 309, and an input output interface (I/O) 311 that may include a bus (not shown). Certain embodiments of the controller portion 302 of the personal defibrillator 66 can include a general-purpose computer, a specific-purpose computer, a microprocessor, a microcontroller, a personal display assistant (PDA), a cellular phone, a wireless communication device, a hard-wired phone, and/or any other known suitable type of communications device, computer, and/or controller that can be implemented in hardware, software, electromechanical devices, and/or firmware. Certain portions of the controller portion 302 of the personal defibrillator 66 can be physically or operably configurable as described with respect to FIGS. 1 to 4. Certain embodiments of the processor 305, as described with respect to FIG. 6, can perform the processing and arithmetic operations such as necessary for defibrillation for certain embodiments of the controller portion 302 of the personal defibrillator 66. Certain embodiments of the controller portion 302 of the personal defibrillator 66 can control the signal processing, database querying and response, computational, timing, data transfer, and other processes associated with certain embodiments of the controller portion 302 of the personal defibrillator 66 as might be associated with defibrillation, monitoring, and other activities.

Certain embodiments of the memory 307 include random access memory (RAM) and read only memory (ROM) that together store the computer programs, operands, and other parameters that control the operation of certain embodiments of the controller portion 302 of the personal defibrillator 66 as might be associated with defibrillation, monitoring, and other activities. The memory 307 can be configurable to contain the defibrillator information and/or individual information obtained, retained, or captured by that particular controller portion 302 of the personal defibrillator 66 as might be associated with defibrillation, monitoring, and other activities.

Certain embodiments of the bus can be configurable to provide for digital information transmissions between the processor 305, circuits 309, memory 307, I/O 311, and/or the image memory or storage device (which may be integrated or removable) as might be associated with defibrillation, monitoring, and other activities. In this disclosure, the memory 307 can be configurable as RAM, flash memory, semiconductor-based memory, of any other type of memory that can be configurable to store data pertaining to images. The bus also connects I/O 311 to the portions of certain embodiments of the controller portion 302 of the personal defibrillator 66 that either receive digital information from, or transmit digital information to other portions of the defibrillator as might be associated with defibrillation, monitoring, and other activities.

Figure 6:
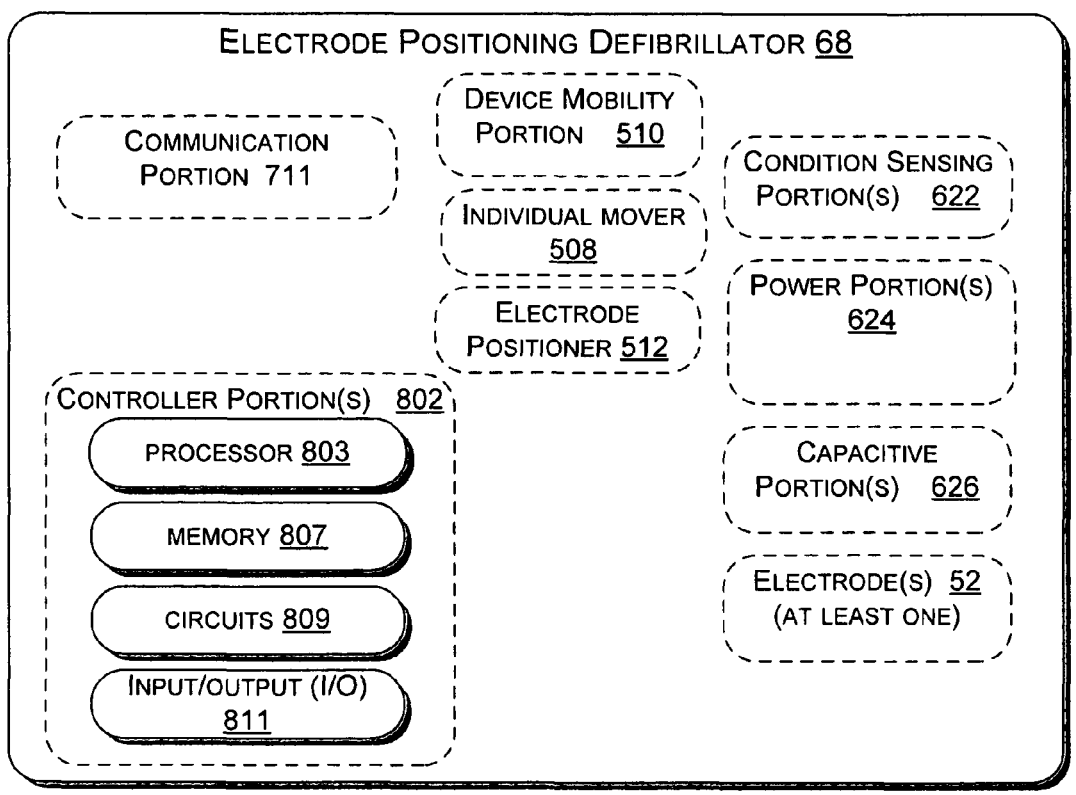
FIG. 6 is block diagram of one embodiment of the electrode positioning defibrillator.

Certain embodiments of the controller portion 302 of the personal defibrillator 66 as described with respect to FIG. 6 can include a transmitter portion (not shown) that can be either included as a portion of certain embodiments of the controller portion 302 of the personal defibrillator 66, or alternately can be provided as a separate unit (e.g., microprocessor-based). In certain embodiments, the transmitter portion can transmit image information between certain embodiments of the controller portion 302 of the personal defibrillator 66 with the shopping device 102 over wired and/or wireless communication links as might be associated with defibrillation, monitoring, and other activities.

Certain embodiments of the controller portion 302 of the personal defibrillator 66, as described with respect to FIG. 6, can include an operation altering portion (not shown) that can be either included as a portion of certain embodiments of the controller portion 302 of the personal defibrillator 66, or alternately can be provided as a separate unit (e.g., microprocessor-based). As such, as defibrillating techniques, voltage, currents, durations, etc. evolve, so can the personal defibrillators.

The memory 307 can provide one example of a memory storage portion. In certain embodiments, the monitored value includes, but is not limited to: a percentage of the memory 307, a number of images that are stored in the memory 307, as might be associated with defibrillation, monitoring, and other activities.

To provide for overflow ability for the memory 307 of certain embodiments of the controller portion 302 of the personal defibrillator 66, the image storage device can be operably coupled to the memory 307 to allow a controllable transmitting of memory data from certain embodiments of the controller portion 302 of the personal defibrillator 66 when the monitored value of data within the memory 307 (e.g., the memory storage portion) exceeds a prescribed value as might be associated with defibrillation, monitoring, and other activities. The prescribed value can include, e.g., some percentage amount or some actual amount of the value as might be associated with defibrillation, monitoring, and other activities.

In certain embodiments, a secondary communication link can be established between the certain embodiments of the controller portion 302 of the personal defibrillator 66 as might be associated with defibrillation, monitoring, and other activities. The secondary communication link can be structured similar to as a communication link, or alternatively can utilize network-based computer connections, Internet connections, etc. to provide data transfer between certain embodiments of the controller portion 302 of the personal defibrillator 66 as might be associated with defibrillation, monitoring, and other activities.

In certain embodiments of the controller portion 302 of the personal defibrillator 66, the particular elements of certain embodiments of the controller portion 302 of the personal defibrillator 66 (e.g., the processor 305, the memory 307, the circuits 309, and/or the I/O 311) can provide a monitoring function to monitor or sense at least one condition of the individual as might be associated with defibrillation, monitoring, and other activities. A monitoring function as provided by certain embodiments of the controller portion 302 of the personal defibrillator 66 can be compared to a prescribed limit, such as whether the number of images contained in the memory 307, the amount of data contained within the memory 307, or some other measure relating to the memory is approaching some value as might be associated with defibrillation, monitoring, and other activities. The limits to the value can, in different embodiments, be controlled by the user or the manufacturer of certain embodiments of the controller portion 302 of the personal defibrillator 66. In certain embodiments, the memory 307 stores motion images, video images, and/or audio images relating to, e.g., a motion picture, camcorder, video, or audio embodiment of certain embodiments of the controller portion 302 of the personal defibrillator 66 as might be associated with defibrillation, monitoring, and other activities. A certain amount of monitoring or other operations may be provided prior to applying defibrillation to ensure that the detected defibrillating condition is a true defibrillating condition.

In certain embodiments, the I/O 311 provides an interface to control the transmissions of digital information between each of the components in certain embodiments of the controller portion 302 of the personal defibrillator 66 as might be associated with defibrillation, monitoring, and other activities. The I/O 311 also provides an interface between the components of certain embodiments of the controller portion 302 of the personal defibrillator 66 as might be associated with defibrillation, monitoring, and other activities. The circuits 309 can include such other user interface devices as a display and/or a keyboard such as can receive input and/or provide information to the individual or other persons as might be associated with defibrillation, monitoring, and other activities.

In other embodiments, the controller portion 302 of the personal defibrillator 66 can be constructed as a specific-purpose computer such as an application-specific integrated circuit (ASIC), a microprocessor, a microcomputer, or other similar devices as might be associated with defibrillation, monitoring, and other activities.

Figure 4:
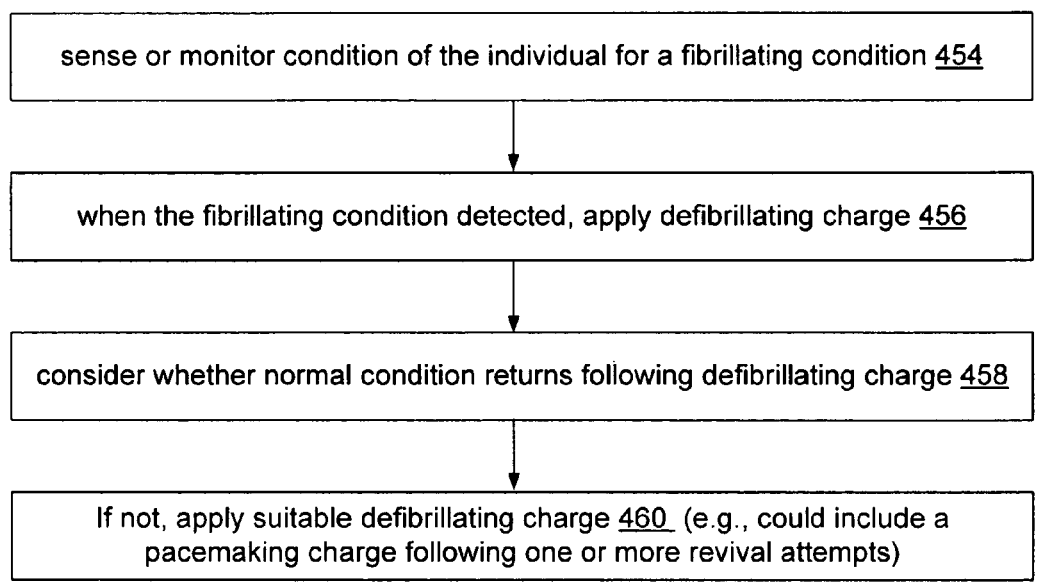
FIG. 4 is a flow chart of operations as could be performed by one embodiment of the personal defibrillator.

Certain embodiments of the personal defibrillator 66 can be configured to follow flowchart, as described with respect to FIG. 4. The logic of FIG. 4 is intended to be illustrative in nature, and not limiting in scope. For example, certain embodiments of the defibrillator can sense for monitor the condition of the individual for a defibrillating condition in 454. For example, a microprocessor-based, mote-based, or other suitable sensor or monitor can sense the fibrillating condition. In 456, when the fibrillating condition is detected, the defibrillating charts can be applied (e.g., using the defibrillator). In 458, following the defibrillating charts, certain embodiments of the defibrillator can consider whether normal conditions return to the individual. For instance, following the defibrillation to the individual 50, the condition of the individual may be considered. In certain embodiments of those instances that the defibrillation is sensed to have been successful, the individual 50 may be queried as to whether they can respond logically and/or how they wish to proceed. If the individual 50 cannot respond logically, in certain embodiments, doctors, emergency care or other people can be notified. In 460, if the individual is not returned at least partially to a normal heart rate, blood flow etc. (e.g., is not revived), in certain embodiments the defibrillator can apply a pacemaking charge to the individual using the defibrillator. For instance, in those instances of the different relation is sensed to have been unsuccessful (e.g. an irregular heartbeat, fibrillation, or heart attack condition is maintained, or the individual 50 has flat-lined or is undergoing a serious heart irregularity), then subsequent defibrillation can be attempted. In certain instances, the subsequent defibrillation can be either another attempt to revive the individual 50, or an attempt to provide the pace making defibrillation to maintain the individual's 50 heartbeat in a regular manner. In certain embodiments, the application of the defibrillation by the personal defibrillator can be controlled by a medically-trained individual or doctor remotely.

A variety of devices, vehicles, locations, etc. could be configured as the potentially apply at least certain embodiments of the personal defibrillator 66. For example, an individual riding in an automobile, truck, bus, aircraft, train, etc. could wear certain embodiments of the personal defibrillator 66. Ambulance workers, ski patrols, life guards, teachers, forest workers, rest-home or hospital workers, etc. could each be provided with their individualized version of the personal defibrillator 66. Using a variety of the electrodes as described in this disclosure which can be configured to apply electrical defibrillation charge for the personal defibrillator 66 through fabric, clothing, etc.

A variety of individuals in vehicles, seats, etc. can also use certain embodiments of the personal defibrillator 66. As such, certain ill patients can be defibrillated on commercial or personal versions of aircraft, cars, trucks, busses, trains, etc. without the necessity to stop and have another person attend to the individual. As such, certain ill patients may be allowed to travel within reach of a defibrillator, which otherwise they would be unable to travel. Certain patients in hospitals, rest homes, doctor offices, etc. can be provided with certain embodiments of the personal defibrillator 66. Individuals using certain embodiments of the personal defibrillator 66 would not have to partially undress during defibrillation; and also they could maintain a somewhat normal lifestyle prior to or following defibrillation, understanding that they could have quick and reliable access to defibrillation.

III. Certain Embodiments of the Electrode Positioning Defibrillator

Figure 5:
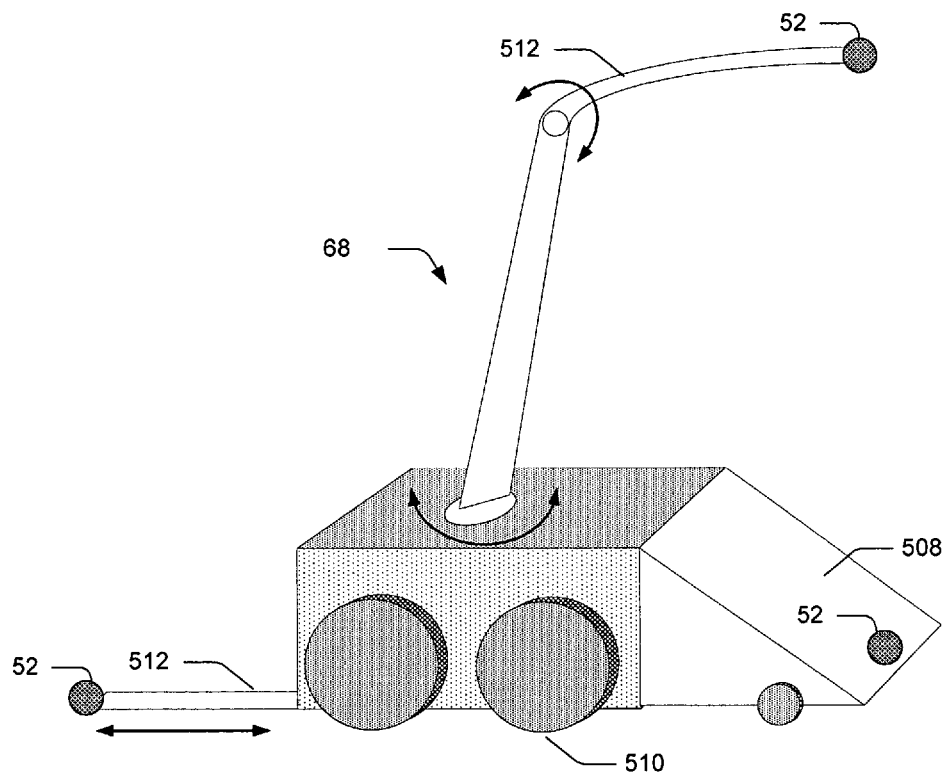
FIG. 5 is a diagram of one embodiment of an electrode positioning defibrillator, similar to as illustrated with respect to FIG. 1.

A detailed description of certain aspects are embodiments of the electrode positioning defibrillator 68 is now described with respect to FIGS. 1 and 5. Certain embodiments of the electrode positioning defibrillator 68 may be configured as, and/or considered to be, a robot or motive-force device to position the electrodes relative to the individual 50. In certain embodiments, the electrode positioning defibrillator can position the individual in a suitable position (either the usual defibrillating position to thereby simplify the defibrillating. In certain embodiments, the suitable individual position for defibrillating can be on the individual's back, or some other position of the individual at which the electrodes can be applied. For example, the individual 50 as illustrated with respect to FIG. 1 may be positioned on their side, on their stomach, or even some other position while being defibrillated. Certain embodiments of the electrode positioning defibrillator 68 can position the electrodes relative to the individual with or without assistance of the individual or from another person (medically trained or other). As such, certain embodiments of the electrode positioning defibrillator 68 operate such that the at least one electrode 52 can be positioned with respect to the individual 50.

A number of features are described with respect to FIG. 5 that can be utilized to position the electrode with respect to the individual 50, as illustrated with respect to FIG. 1. Certain embodiments of the electrode positioning defibrillator 68 can include the device mobility portion 510, an individual mover 508, and/or an electrode positioner 512. Certain embodiments of the device mobility portion 510 are configured with sufficient power and/or capabilities to move the electrode positioning defibrillator 68 into positioned such that it can interface with the individual. Certain embodiments of the device mobility portion 510 may be configured with sufficient power and/or capabilities to be able to move the individual 50, such as by rolling the individual 50 over into the usual defibrillating position. Certain embodiments of the device mobility portion 510 are configured with sufficient power and/or capabilities to either slide the electrode 52 underneath the individual, or position the electrode 52 relative to the individual. As such, he should be understood that certain embodiments of the device mobility portion 510 can be relatively strong depending upon the intended defibrillating task that can be performed. Certain embodiments of the device mobility portion 510 can utilize wheels (at least one drive wheel), treads, legs, and other suitable mobility mechanisms such as are known in the robotic and mobility device technologies.

Certain embodiments of the arrows positioned proximate certain of the electrode positioner 512 of FIG. 5 are intended to be illustrative in nature and not limiting in scope. For instance, the electrode positioner 512 as illustrated to the left of FIG. 5 is shown with a straight arrow. As such, in certain embodiments the electrode positioner 512 can extend, retract, or telescope to the left or right with respect to FIG. 5. Alternatively, certain embodiments of the drive mobility portion 510 can drive certain embodiments of the electrode positioner 512 to the right or left as illustrated with respect to FIG. 5. Alternately, other rotational, torsional, axial, other, or combinational motion(s) can be provided to/by certain embodiments of the electrode positioner 512 since the illustrated motions are intended to be illustrative in nature but not limiting in scope. Therefore, certain embodiments of the electrode positioner 512 can be considered as a device or mechanism that can position the at least one electrode with respect to the individual using its own force and/or control, force and/or control provided by the drive mobility portion, and. Or force or control provided by some other portion, device, or mechanism.

While the embodiment of the electrode positioning defibrillator 68 as described with respect to FIGS. 1 and 5 can be configured as a devoted robotic or motive-applying device, it is envisioned that certain embodiments of the electrode positioning defibrillator can be applied to a variety of existing devices, vehicles, mechanisms, etc. For example, certain embodiments of automated or robotic floor cleaners and/or automated or robotic vacuum cleaners could each integrate the electrode positioning defibrillator 68. Certain embodiments of the automated or robotic floor cleaners and/or the automated or robotic vacuum cleaners can even be configured with a wedge-shaped individual mover 508, which could for example be used to roll over an unconscious individual to a more suited position for defibrillation.

Certain embodiments of the electrode positioning defibrillator 68 can include an individual mover 508, such as a wedge that can be driven under the individual 50, and thereby reposition the individual into a usual defibrillating position (or an unusual defibrillating position in which defibrillation can be applied). Certain embodiments of the individual mover 508 can include an integrated version of the electrode 52 as illustrated in FIG. 5, which can be configured as described in this disclosure to provide defibrillation with the individual wedged against certain embodiments of the individual mover 508.

Certain embodiments of the electrode positioner 512 can also be configured to slide the electrode 52 under the individual (e.g., that electrode positioner 512 to the left of the electrode positioning defibrillator 68, as illustrated with respect to FIG. 5). For instance, the electrode 52 can be driven at least partially using the device mobility portion 510 under the individual. Alternatively, certain embodiments of the electrode positioner shown to the left in FIG. 5 can be extended using a variety of extension and/or telescoping mechanisms to thereby drive the electrode under the individual. Certain embodiments of the electrode positioner 512 can thereby utilize force of the device mobility portion 510 to drive the electrode positioner under the individual.

Other embodiments of the electrode positioner 512 can be configured to displace the electrode 52 with respect to the individual 50 (e.g., that electrode positioner 512 above the electrode positioning defibrillator 68, as illustrated with respect to FIG. 5). For instance, certain embodiments of the electrode positioner 512 can include a variety of linkage and/or rotative elements to position the electrode to a desired location. As such, any mechanism that can be used to displace the electrode (typically utilizing a suitable force), can be utilized as an embodiment of the electrode positioner.

Certain embodiments of the electrode positioning defibrillator 68 can also include a condition sensing portion 622, a power portion 624, a capacity of portion 626, the at least one electrode 52, a communication portion 711, and/or a controller portion 802. Certain embodiments of the communication portion 711 can communicate with other devices, computers, controllers, persons, etc. relating to defibrillation. As such, in certain instances, another device such as the personal defibrillator 66 might be in a suitable position to evaluate whether the individual is in need of defibrillation. As such, certain embodiments of the personal defibrillator 66 can communicate utilizing their communication portion 319, as described with respect to FIG. 3, to the communication portion 711 of the electrode positioning defibrillator 68. As such, a variety of networking techniques and/or technologies can be utilized to evaluate whether the individual should be defibrillated.

Certain embodiments of the electrode positioning defibrillator 68 can utilize the condition sensing portion 622 to determine, with or without assistance from another device or person, whether the individual should be defibrillated. Certain embodiments of the condition sensing portion 622 can determine whether the individual 50 is having a heart or circulatory condition that can utilize defibrillation. Examples of such heart or circulatory condition can include, but is not limited to, a heart attack, a heart rate irregularity, a heart fibrillation, a heart-pumping reduction, a fibrillation, and/or an other condition that indicate that the individual's heart is not operating as desired and/or should be revived. A variety of techniques may be utilized since the conditions at least partially utilizing the condition sensing portion 622 can include, but is not limited to, blood-pressure monitors or blood flow monitors (which may utilize acoustic, electronic, optical, electromagnetic, or other technology). Other techniques that can be used to assess whether the individual 50 should be defibrillated can include a consciousness indicator (e.g., the individual passes out), and individual response indicator, input of the individual or another person to indicate that the individual may be in need of defibrillation, etc.

Certain embodiments of the power portion 624 can be utilized to provide the power to the electrode positioning defibrillator 68, as well as the power associated with the defibrillating charge. In certain embodiments, the power portion 624 can include a battery or other electrical source that is sufficient to establish the defibrillating charge either directly and/or via the capacitor portion 626. The voltages and/or current associated with the defibrillating charge to vary depending upon the type of defibrillating charge. For example, defibrillating an individual to revive them from a heart attack would require a relatively high voltage, while defibrillating and individual to provide pacemaking would acquire considerably lower voltage.

Certain embodiments of the personal defibrillator can include the capacitor portion 626 that can allow the first is as provided by the power portion 342 to increase to a greater level them that normally plotted by the power portion, to affect a relatively high-voltage defibrillation. As such, for example, a relatively small battery such as one that can power consumer-electronics type device can utilize the capacitor portion 626 to provide a sizable defibrillation charge. Certain embodiments of the defibrillation charge are associated with a considerable voltage, and a relatively small current and duration. As such, certain embodiments of the capacitor portion 626 can be configured to provide a suitable electrical voltage, current, and/or duration capability for the particular desired defibrillating charge. Certain embodiments of the electrode positioning defibrillator 68 can utilize similar electrode(s), and/or electrode techniques, as described with respect to the personal defibrillator 66 and/or a generalized defibrillator.

Certain embodiments of the electrode positioning defibrillator 68 can be computer based, mote based, and/or electronics based. As described within this disclosure, multiple ones of the different embodiments of the electrode positioning defibrillator 68 can transfer information about the individual 50 or their condition, image information, data, signals, etc. via a communication link to or from the remote monitoring location 330 or some intermediate device as might be associated with defibrillation, monitoring, and other activities. One embodiment of the controller portion 802 can include a processor 803 such as a central processing unit (CPU), a memory 807, a circuit or circuit portion 809, and an input output interface (I/O) 811 that may include a bus (not shown). Certain embodiments of the controller portion 802 of the electrode positioning defibrillator 68 can be a general-purpose computer, a specific-purpose computer, a microprocessor, a microcontroller, a personal display assistant (PDA), a cellular phone, a wireless communication device, a hardwired phone, and/or any other known suitable type of communications device, computer, and/or controller that can be implemented in hardware, software, electromechanical devices, and/or firmware. Certain portions of the controller portion 802 of the electrode positioning defibrillator 68 can be physically or operably configurable as described with respect to FIG. 6 as might be associated with defibrillation, monitoring, and other activities. Certain embodiments of the processor 803 as described with respect to FIG. 6 can perform the processing and arithmetic operations for certain embodiments of the controller portion 802 of the electrode positioning defibrillator 68. Certain embodiments of the controller portion 802 of the electrode positioning defibrillator 68 can control the signal processing, database querying and response, computational, timing, data transfer, and other processes associated with certain embodiments of the controller portion 802 of the electrode positioning defibrillator 68.

Certain embodiments of the memory 807 include random access memory (RAM) and read only memory (ROM) that together store the computer programs, operands, and other parameters that control the operation of certain embodiments of the controller portion 802 of the electrode positioning defibrillator 68. The memory 807 can be configurable to contain the defibrillation information or individual information obtained, retained, or captured by that particular controller portion 802 of the electrode positioning defibrillator 68.

Certain embodiments of the bus can be configurable to provide for digital information transmissions between the processor 803, circuits 809, memory 807, I/O 811, and/or the image memory or storage device (which may be integrated or removable). In this disclosure, the memory 807 can be configurable as RAM, flash memory, semiconductor-based memory, of any other type of memory that can be configurable to store data pertaining to images. The bus also connects I/O 811 to the portions of certain embodiments of the controller portion 802 of the electrode positioning defibrillator 68 that either receive digital information from, or transmit digital information to other portions of the electrode positioning defibrillator 68.

Certain embodiments of the controller portion 802 of the electrode positioning defibrillator 68 as described with respect to FIG. 6 includes a transmitter portion (not shown) that can be either included as a portion of certain embodiments of the controller portion 802 of the electrode positioning defibrillator 68, or alternately can be provided as a separate unit (e.g., microprocessor-based). In certain embodiments, the transmitter portion can transmit image information between certain embodiments of the controller portion 802 of the electrode positioning defibrillator 68.

Certain embodiments of the controller portion 802 of the electrode positioning defibrillator 68 as described with respect to FIG. 6 includes an operation altering portion (not shown) that can be either included as a portion of certain embodiments of the controller portion 802 of the electrode positioning defibrillator 68, or alternately can be provided as a separate unit (e.g., microprocessor-based). Examples of operation altering portions include, but are not limited to, altering a resolution, altering a contextual library, altering an aspect ratio, altering a color intensity and/or brightness or particular defibrillators.

The memory 807 can provide one example of a memory storage portion. In certain embodiments, the monitored value includes, but is not limited to: a percentage of the memory 807, a number of images that are stored in the memory 807, or for motion images a recording interval (audio or video recording intervals).

To provide for overflow ability for the memory 807 of certain embodiments of the controller portion 802 of the electrode positioning defibrillator 68, the image storage device can be operably coupled to the memory 807 to allow a controllable transmitting of memory data from certain embodiments of the controller portion 802 of the electrode positioning defibrillator 68 when the monitored value of data within the memory 807 (e.g., the memory storage portion) exceeds a prescribed value. The prescribed value can include, e.g., some percentage amount or some actual amount of the value.

In certain embodiments, a secondary communication link can be established between the certain embodiments of the controller portion 802 of the electrode positioning defibrillator 68. The secondary communication link can be structured similar to as a communication link, or alternatively can utilize network-based computer connections, Internet connections, etc. to provide information and/or data transfer between certain embodiments of the controller portion 802 of the electrode positioning defibrillator 68.

In certain embodiments of the controller portion 802 of the electrode positioning defibrillator 68, the particular elements of certain embodiments of the controller portion 802 of the electrode positioning defibrillator 68 (e.g., the processor 803, the memory 807, the circuits 809, and/or the I/O 811) can provide a monitoring function to monitor or sense at least one condition of the individual. A monitoring function as provided by certain embodiments of the controller portion 802 of the electrode positioning defibrillator 68 can be compared to a prescribed limit, such as whether the number of images contained in the memory 807, the amount of data contained within the memory 807, or some other measure relating to the memory is approaching some value. The limits to the value can, in different embodiments, be controlled by the user or the manufacturer of certain embodiments of the controller portion 802 of the electrode positioning defibrillator 68. In certain embodiments, the memory 807 stores motion images, video images, and/or audio images relating to, e.g., a motion picture, camcorder, video, or audio embodiment of certain embodiments of the controller portion 802 of the electrode positioning defibrillator 68.

In certain embodiments, the I/O 811 provides an interface to control the transmissions of digital information between each of the components in certain embodiments of the controller portion 802 of the electrode positioning defibrillator 68 and the shopping device 102. The I/O 811 also provides an interface between the components of certain embodiments of the controller portion 802 of the electrode positioning defibrillator 68 and the shopping device 102. The circuits 809 can include such other user interface devices as a display and/or a keyboard.

In other embodiments, the controller portion 802 of the electrode positioning defibrillator 68 can be constructed as a specific-purpose computer such as an application-specific integrated circuit (ASIC), a microprocessor, a microcomputer, or other similar devices.

A variety of devices could be configured as the electrode positioning defibrillator 68. For example, a portion of an automobile (either internal or external) could be provided with certain embodiments of the individual mover 508, and/or certain embodiments of the electrode positioner 512. A trained dog (such as used in ski patrols, etc.) could be fitted with certain embodiments of the electrode positioning defibrillator, and allowed to run to those in need of defibrillation. Hospitals, care centers, schools, ski patrols, life guards, workplaces, ambulance workers, forest workers, etc. could each be provided with their individualized version of the electrode positioning defibrillator. Using a variety of the electrodes as described in this disclosure which can be configured to apply electrical defibrillation charge through fabric, clothing, etc.

A variety of vehicles, seats, etc. can also be configured with certain embodiments of the electrode positioning defibrillator 68. For instance, in vehicles seat belts can be configured with electrodes that can extend through the clothing. As such, certain potentially ill patients can be defibrillated on commercial or personal versions of aircraft, cars, trucks, busses, trains, etc. without the necessity to stop and have another person attend to the individual. Certain hospitals, rest homes, doctor offices, etc. can be provided with certain embodiments of the electrode positioning defibrillator 68 Individuals using certain embodiments of the electrode positioning defibrillator 68 would not have to partially undress, and as such could maintain a somewhat normal lifestyle.

IV. Certain Embodiments of the Defibrillator Electrode(s)

Figure 10:
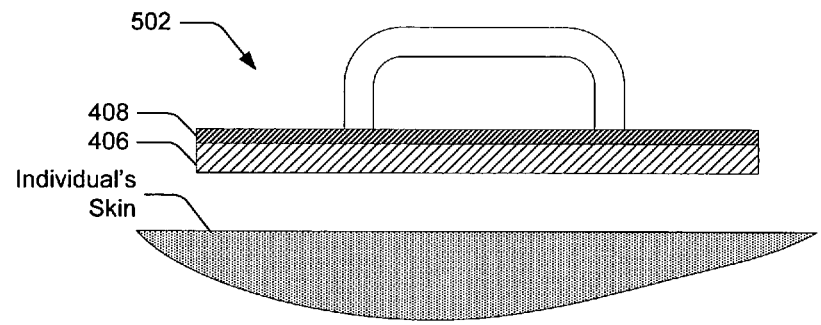
FIG. 10 is a cross sectional view of one embodiment of an electrode.
Figure 11:
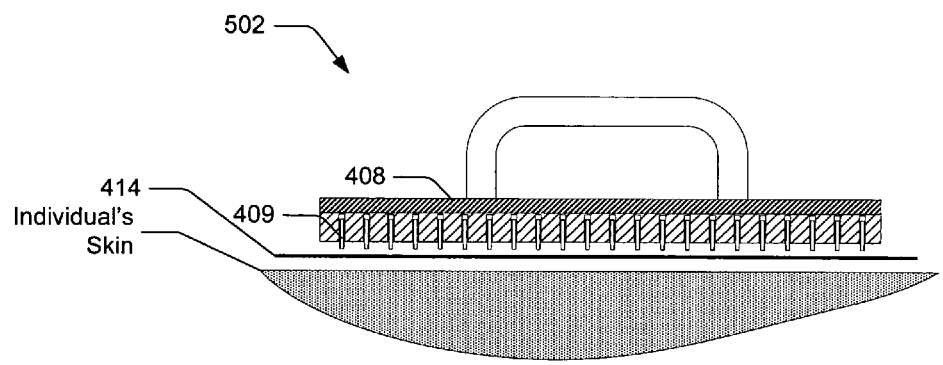
FIG. 11 is a cross sectional view of another embodiment of the electrode.
Figure 12:
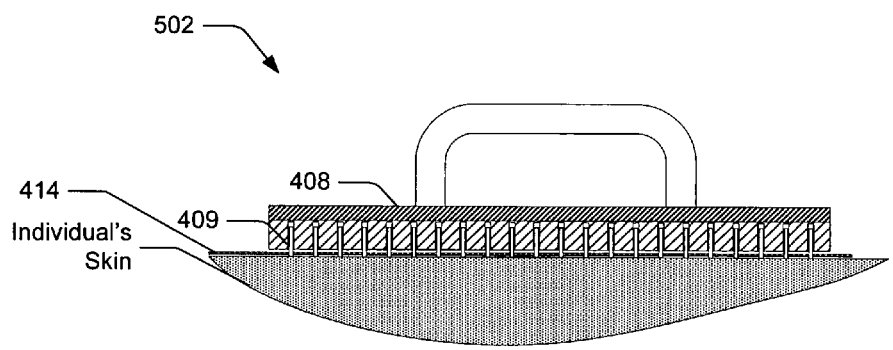
FIG. 12 is a cross sectional view of the embodiment of the electrode in FIG. 11 as pressed against skin of an individual.

Certain embodiments of the at least one defibrillator electrodes are described with respect to FIGS. 10, 11, and 12. While certain embodiments of the at least one electrode(s) are traditionally understood as being utilized in pairs, it is envisioned that one electrode may be applied to an individual 50 under certain instances. For example, a defibrillator that is electrically grounded may apply a single electrode to the chest cavity of the individual 50 having a remote portion (e.g., their rib cage, back, etc.) that is also grounded. As such, by using a single electrode, a grounded embodiment of the defibrillator may form a complete electrical path through the individual 50, and thereby apply the defibrillating charge.

One aspect of certain embodiments of the at least one electrode 52 is that they can be applied over clothing, and apply the defibrillation through the clothing and/or through holes formed in the clothing. As such, certain embodiments of the personal defibrillator 66, electrode positioning defibrillator 68, and/or other automated defibrillators that utilize the at least one electrode 52 can be used with the patient clothed. As such, defibrillation can be provided (and fibrillating state can be sensed and/or monitored) in very public situations and without considerably altering the lifestyle of the individual.

In addition, the process or techniques of applying this electrodes may differ, and as such, only one electrode may be applied by the defibrillator in a particular manner, and as such, only one electrode may have a particular configuration are characteristic as described in this disclosure. For instance, one electrode may be situated in a position underneath where the individual 50 is currently situated, while another is more easily accessible. As such, the techniques to apply the different electrode may differ considerably, and as such to configuration of the particular electrodes may also differ. It is likely that many embodiments of the defibrillator would utilize two, or more, electrodes to apply the defibrillating charge, as is understood with traditional defibrillation techniques and/or systems.

One embodiment of the at least one electrode(s) 52 can be configured to include an electrically conductive layer 406 disposed substantially adjacent to electrically insulating layer 408. In certain embodiments as described with respect to FIG. 10, the electrically conductive layer 406 can be substantially planar, and as such, can afford a relatively large area of electric contact with the individual's 50 skin when put in contact with the individual's skin. In certain embodiments, the electrically insulating layer 408 can be configured to electrically insulate other people attempting to apply the at least one electrode(s) 52, and as such may be closely conforming to the electrically conductive layer 406. In certain embodiments, the electrically insulating layer 408 may even be adhered to, connected to, or otherwise associated with the electrically conductive layer 406.

Certain embodiments of the at least one electrode(s) 52 can be physically applied with manual pressure to the individual 50 (such as with the handle). In certain instances, either medical personnel, the individual 50, or other people could apply the at least one electrode(s) 52. Certain embodiments of the at least one electrode(s) 52 can be adhered to, pressed against, maintained in position, or otherwise positioned relative to the individual 50 using tape, bandages, securing strips, or other similar mechanisms. By maintaining certain embodiments of the at least one electrode(s) 52 in contact with the skin of the individual 50, electrical conductivity can be applied by the defibrillator to affect the defibrillation.

Certain embodiments of the at least one electrode(s) 52 can include at least one extensible electric contact(s) 409 as described with respect to FIGS. 11 and 12. It is desirable as certain embodiments of the at least one extensible electric contact(s) 409 can be configured to extend through the material 414 (of the clothing, etc.) being worn by the individual 50, and provide electric contact directly to the skin of the individual 50. In other embodiments, even though the extensible electric contact(s) 409 do not pass through the material or fabric 414 being worn by the individual, the pressure exerted against the material or fabric is sufficiently concentrated (due to the relatively small sizes of the extensible electrical contact (s) 409), to provide electrical flow across the material to the individual's skin. Certain embodiments of the extensible electrical contact(s) 409 have sufficient contact area with the skin of the individual 50 to allow for the defibrillating charge to be applied by the defibrillator to the individual 50. Certain embodiments of the at least one extensible electric contact(s) 409 can be configured as an extensible needle, an extensible wedge, an extensible pointer, or another suitable pressure-concentrating configuration, etc. As such, the selection of the material, the extensible needle, an extension force of the extensible contact(s), etc. can be utilized to determine whether the extensible contact(s) can extend through the materials of the clothing, etc., or whether the defibrillating charge is applied through the clothing.

Certain embodiments of the at least one extensible electric contact(s) 409 can be biased into electric contact with the skin only when actuated, or in other embodiments on a continual basis. The biasing of the at least one extensible electric contact(s) 409 may, in certain instances, include biasing the extensible electric contact(s) through the material 414 covering the individual's 50 skin. As such, the at least one extensible electric contact(s) 409 can provide sufficient electrical contact for the at least one electrode(s) 52 to the individual's 50 skin.

Certain embodiments of the at least one extensible electric contact(s) 409 can be configured to extend through different types of materials 414. For instance, certain embodiments of the at least one electrode(s) 52 can be sewn into garments to be worn by the individual 50, belts or harnesses to be worn by the individual, taped in the position onto the individual, or held by the individual or another person to allow the at least one extensible electric contact(s) 409 to extend into contact with the individual's 50 skin when biased. As such, certain embodiments of the extensible electric contact(s) can be configured differently and can operate differently.

Certain embodiments of the at least one extensible electric contact(s) 409 can utilize a variety of biasing techniques that can include, but are not limited to, springs, electromechanical devices, force generating devices, etc. The configuration of certain embodiments of the at least one extensible electric contact(s) 409, as well as the force they can be applied thereto during biasing, should be selected to ensure sufficient defibrillating electrical contact can be provided, while not seriously hurting the individual 50. Certain embodiments of the at least one electrode(s) 52 can thereby be configured such that a person or medical personnel could apply the at least one extensible electric contact(s) 409 through the fully clothed individual 50. As such, a person attempting to apply defibrillation to the individual 50 using certain embodiments of the at least one electrode(s) 52 having the one or more extensible electric contact(s) 409 may not have to remove the clothing of the individual 50 might have you be removed during defibrillation and many typical defibrillators, thereby possibly saving valuable resuscitation time.

V. Certain Embodiments of Defibrillators with Relevant Flowcharts

Within the disclosure, flow charts of the type described in this disclosure apply to method steps as performed by a computer or controller. The flow charts can also apply to apparatus devices, such as an antenna or a node associated therewith that can include, e.g., a general-purpose computer or specialized-purpose computer whose structure along with the software, firmware, electromechanical devices, and/or hardware, can perform the process or technique described in the flow chart.

Figure 7A:
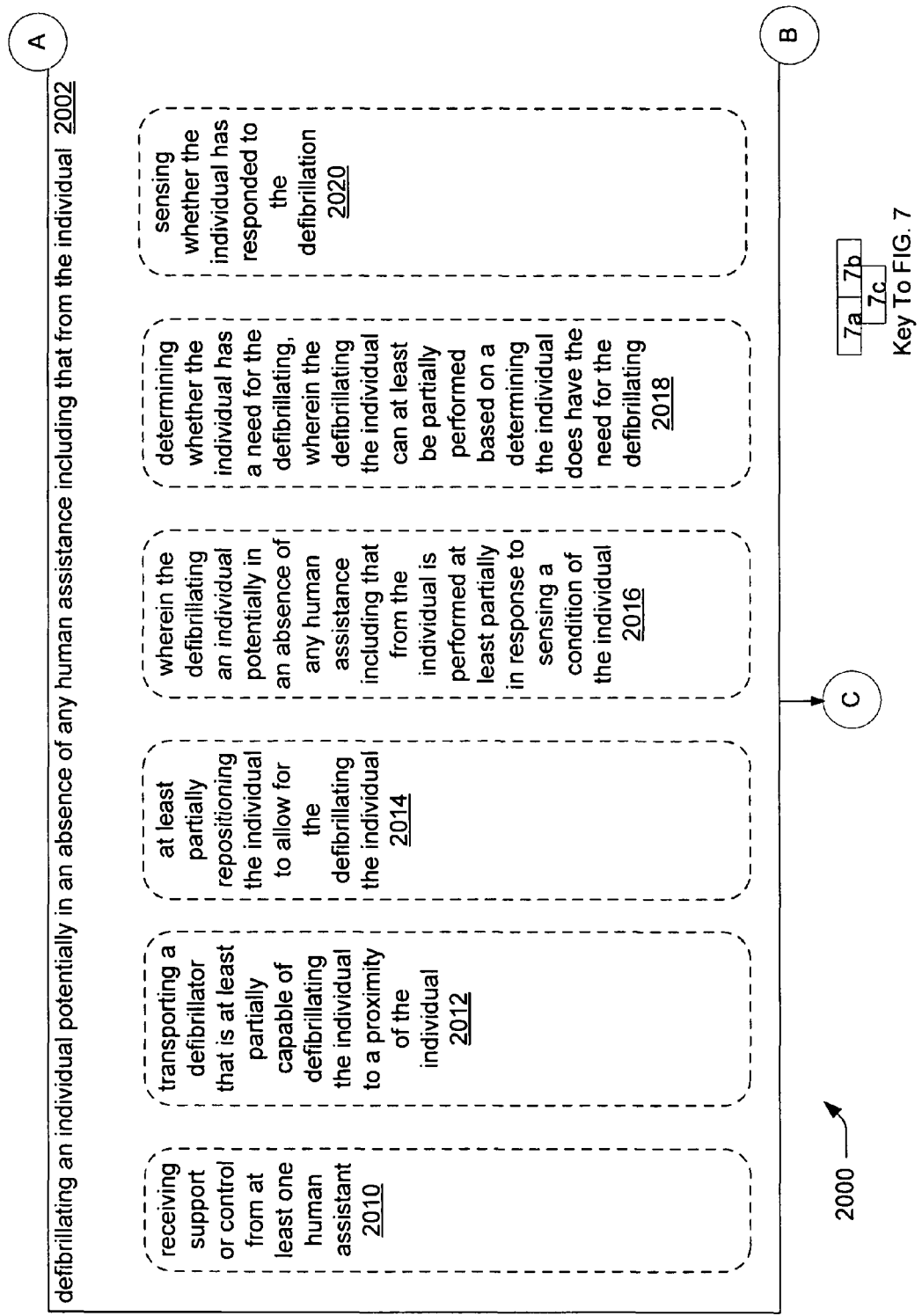
Figure 7B:
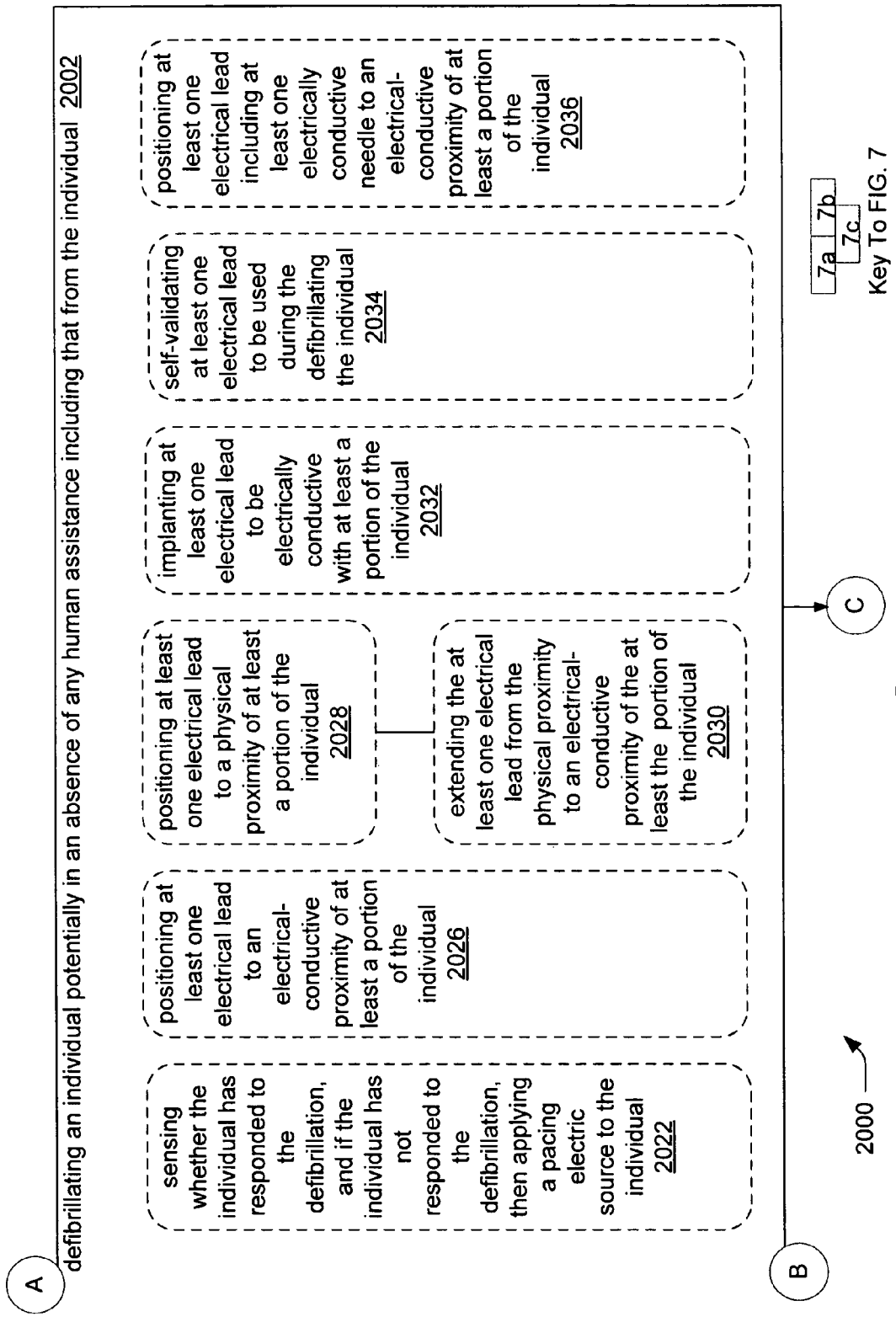

One embodiment of a high-level flowchart of a defibrillation technique 2000 as described with respect to FIG. 7 (including FIGS. 7*a*, 7*b*, and 7*c*) and includes, but is not limited to, operations 2002 and optional operations 2006 and/or 2008. One embodiment of operation 2002 can include, but is not limited to, optional operations 2010, 2012, 2014, 2016, 2018, 2020, 2022, 2026, 2028, 2030, 2032, 2034, and/or 2036. The high-level flowchart of FIG. 7 (including FIGS. 7*a*, 7*b*, and 7*c*) should be considered in combination with the embodiment of the defibrillation mechanism 100, as described with respect to FIGS. 1 to 6. One embodiment of operation 2002 can include, but is not limited to, defibrillating an individual potentially in an absence of any human assistance including that from the individual. One embodiment of the defibrillating an individual potentially in an absence of any human assistance including that from the individual of operation 2002 can include operation 2010, that can include, but is not limited to, receiving support or control from at least one human assistant. For example, the personal defibrillator 66 as described with respect to FIGS. 1 to 4, and the electrode positioning defibrillator 66 as described with respect to FIGS.

1, 5, and/or 6 can defibrillate the individual even without the assistance of the individual, or any other people. One embodiment of the defibrillating an individual potentially in an absence of any human assistance including that from the individual of operation 2002 can include operation 2012, that can include, but is not limited to, transporting a defibrillator that is at least partially capable of defibrillating the individual to a proximity of the individual. For example, the defibrillator can transport itself to the individual. One embodiment of the defibrillating an individual potentially in an absence of any human assistance including that from the individual of operation 2002 can include operation 2014, that can include, but is not limited to, at least partially repositioning the individual to allow for the defibrillating the individual. For example, certain embodiments of the individual mover 508 as described with respect to FIGS. 5 and/or 6 can roll the individual over, such as to be able to position the at least one electrode. One embodiment of operation 2016 can include, but is not limited to, wherein the defibrillating an individual potentially in an absence of any human assistance including that from the individual of operation 2002 is performed at least partially in response to sensing a condition of the individual. For example, the defibrillator can defibrillator to at least partially in response to sensing the individual's condition from, e.g., a microprocessor or mode-based sensor and/or the condition sensing portion as described with respect to FIGS. 3 and/or 6. One embodiment of the defibrillating an individual potentially in an absence of any human assistance including that from the individual of operation 2002 can include operation 2018, that can include, but is not limited to, determining whether the individual has a need for the defibrillating, wherein the defibrillating the individual can at least be partially performed based on a determining the individual does have the need for the defibrillating. For example, the defibrillation is at least partially performed based upon a determination that the individual has the need for the defibrillation. One embodiment of the defibrillating an individual potentially in an absence of any human assistance including that from the individual of operation 2002 can include operation 2020, that can include, but is not limited to, sensing whether the individual has responded to the defibrillation. For example, the individual can be monitored following the defibrillation to determine whether they have responded to the defibrillation. One embodiment of the defibrillating an individual potentially in an absence of any human assistance including that from the individual of operation 2002 can include operation 2022, that can include, but is not limited to, sensing whether the individual has responded to the defibrillation, and if the individual has not responded to the defibrillation, then applying a pacing electric source to the individual. For example, the individual can be monitored following the defibrillation to determine whether they have responded to the defibrillation, and if they have not, then the defibrillator can apply a pacing electric source similar to as with commercially-available pacemakers. One embodiment of the defibrillating an individual potentially in an absence of any human assistance including that from the individual of operation 2002 can include operation 2026, that can include, but is not limited to, positioning at least one electrical lead to an electrical-conductive proximity of at least a portion of the individual. For example, positioning the electrical lead within the electrical-conductive proximity of the individual, such as on the skin of the individual. One embodiment of the defibrillating an individual potentially in an absence of any human assistance including that from the individual can include operations 2028 and/or 2030. Certain embodiments of operation 2028 can include, but is not limited to, positioning at least one electrical lead to a physical proximity of at least a portion of the individual. For example, positioning the electrical lead within a close physical proximity of the individual, such as on or close to the skin of the individual. Certain embodiments of operation 2030 can include, but is not limited to, extending the at least one electrical lead from the physical proximity to an electrical-conductive proximity of the at least the portion of the individual. For example, extending the electrical lead to within the electrical-conductive proximity of the at least a portion of the individual. One embodiment of the defibrillating an individual potentially in an absence of any human assistance including that from the individual of operation 2002 can include operation 2032, that can include, but is not limited to, implanting at least one electrical lead to be electrically conductive with at least a portion of the individual. For example, implanting the electrical lead into the individual. One embodiment of the defibrillating an individual potentially in an absence of any human assistance including that from the individual of operation 2002 can include operation 2034, that can include, but is not limited to, self-validating at least one electrical lead to be used during the defibrillating the individual. For example, self-validating the electrical lead such as to insure its proper operation. One embodiment of the defibrillating an individual potentially in an absence of any human assistance including that from the individual of operation 2002 can include operation 2036, that can include, but is not limited to, positioning at least one electrical lead including at least one electrically conductive needle to an electrical-conductive proximity of at least a portion of the individual. For example, positioning the electrically conductive needle of the electrical lead into the electrical-conductive proximity of the leased a portion of the individual. One embodiment of optional operation 2006 can include, but is not limited to, wherein the individual includes a person. For example, the individual as human. One embodiment of optional operation 2008 can include, but is not limited to, wherein the individual includes an animal. For example, the individual is not human, but an animal. The order of the operations, methods, mechanisms, etc. as described with respect to FIG. 7 (including FIGS. 7a, 7b, and 7c) is intended to be illustrative in nature, and not limited in scope.

One embodiment of a high-level flowchart of an defibrillator technique 2200 as described with respect to FIG. 8 and includes, but is not limited to, operations 2202 and/or 2204 and/or optional operations 2212. One embodiment of operation 2202 can include, but is not limited to, optional operation 2210. The high-level flowchart of FIG. 8 should be considered in combination with the embodiment of the defibrillation mechanism 100, as described with respect to FIGS. 1 to 6. One embodiment of operation 2202 can include, but is not limited to, positioning an electrode in electrical proximity to an individual when the individual is in an unusual defibrillating position. For example, allowing the electrode to be electoral proximity of the individual who is not in the usual defibrillating position (e.g., lying on their back). As such, defibrillation can be applied to individuals that are not lying on their back. One embodiment of operation 2204 can include, but is not limited to, applying a defibrillating charge to the individual at least partially via the electrode when the individual is in the unusual defibrillating position. For example, applying the defibrillating charge to the individual at least partially via the electrode. One embodiment of the positioning an electrode in electrical proximity to an individual when the individual is in an unusual defibrillating position of operation 2202 can include operation 2210, that can include, but is not limited to, extending at least a portion of the electrode through a clothing of the individual. For example, extending at least the portion of the electrode (e.g., a needle, probe, etc.) adjacent to or through clothing of the individual. One embodiment of operation 2212 can include, but is not limited to, displacing the individual into a usual defibrillating position. For example, displacing the individual from the unusual defibrillating position to the usual defibrillating position using, for example, certain embodiments of the electrode positioning device as described with respect to FIGS. 1, 5, and/or 6. The order of the operations, methods, mechanisms, etc. as described with respect to FIG. 8 is intended to be illustrative in nature, and not limited in scope.

Figure 9:
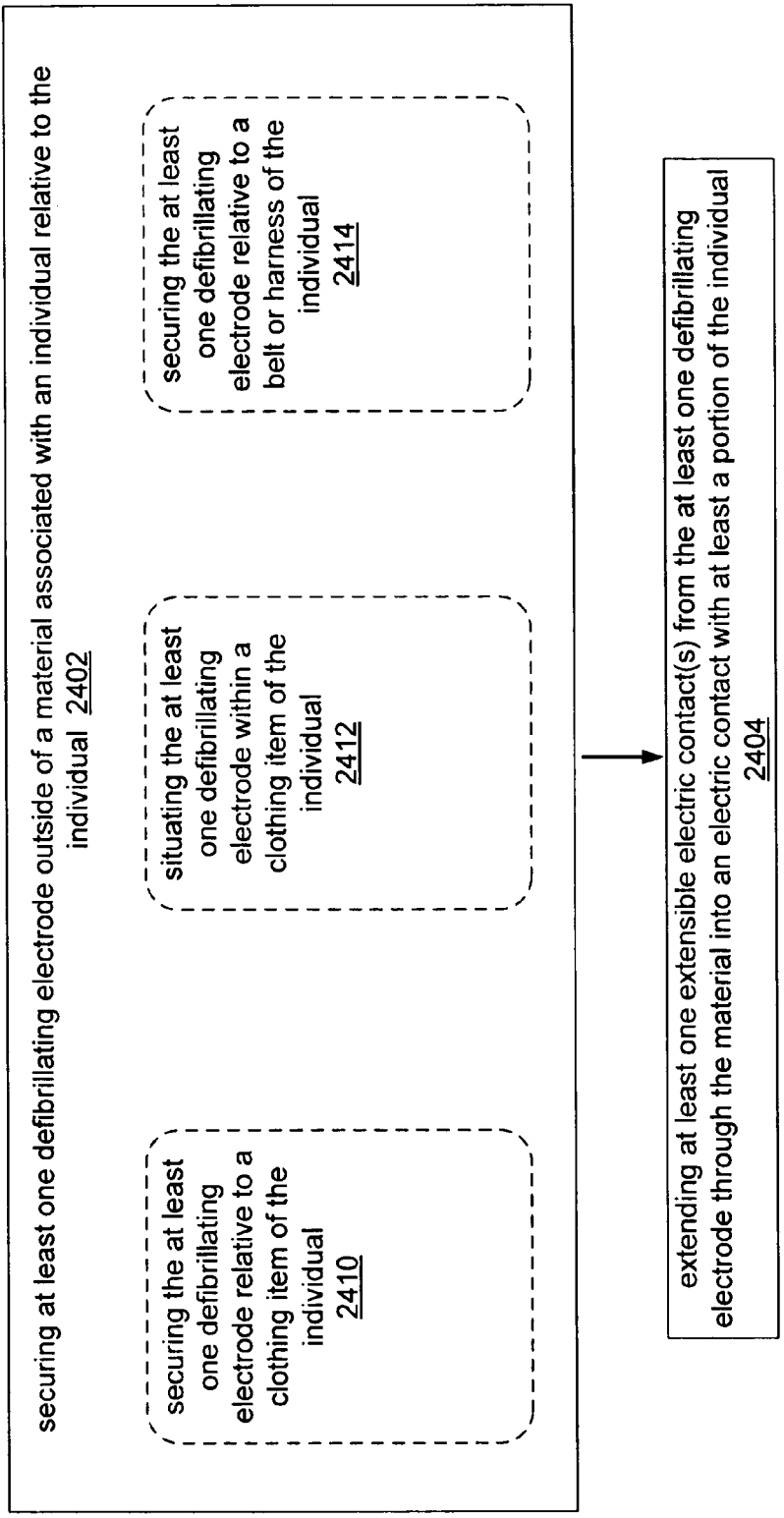
FIG. 9 is one embodiment of a flow chart of an operation as could be performed by one embodiment of the defibrillator.

One embodiment of a high-level flowchart of a defibrillator technique 2400 as described with respect to FIG. 9 and includes, but is not limited to, operations 2402 and/or 2404. One embodiment of operation 2402 can include, but is not limited to, optional operations 2410, 2412, and/or 2414. The high-level flowchart of FIG. 9 should be considered in combination with the embodiment of the defibrillation mechanism 100, as described with respect to FIGS. 1 to 6. One embodiment of operation 2402 can include, but is not limited to, securing at least one defibrillating electrode outside of a material associated with an individual relative to the individual. For example, securing of the defibrillating electrode outside the clothing of the individual. One embodiment of operation 2404 can include, but is not limited to, extending at least one extensible electric contact(s) from the at least one defibrillating electrode through the material into an electric contact with at least a portion of the individual. For example, extending the at least one extensible electric contacts of the defibrillating electrode through the material to electrically contact the individual. One embodiment of the securing at least one defibrillating electrode outside of a material associated with an individual relative to the individual of operation 2402 can include operation 2410, that can include, but is not limited to, securing the at least one defibrillating electrode relative to a clothing item of the individual. For example, securing the defibrillating electrode relative to clothing of the individual. One embodiment of the securing at least one defibrillating electrode outside of a material associated with an individual relative to the individual of operation 2402 can include operation 2412, that can include, but is not limited to, situating the at least one defibrillating electrode within a clothing item of the individual. For example, situating the defibrillating electrode within clothing of the individual, such as within a pocket or zone within a seam, etc. One embodiment of the securing at least one defibrillating electrode outside of a material associated with an individual relative to the individual of operation 2402 can include operation 2414, that can include, but is not limited to, securing the at least one defibrillating electrode relative to a belt or harness of the individual. For example, securing the defibrillating electrode to the belt or harness that can be worn by the individual. The order of the operations, methods, mechanisms, etc. as described with respect to FIG. 9 is intended to be illustrative in nature, and not limited in scope.

In one or more various aspects, related systems include but are not limited to circuitry and/or programming for effecting the herein-referenced method aspects; the circuitry and/or programming can be virtually any combination of hardware, software, electromechanical system, and/or firmware configurable to effect the herein-referenced method aspects depending upon the design choices of the system designer.

VI. Conclusion

This disclosure provides a number of embodiments of the defibrillator. The embodiments of the defibrillator as described with respect to this disclosure are intended to be illustrative in nature, and are not limiting its scope.

Those having skill in the art will recognize that the state of the art has progressed to the point where there is little distinction left between hardware, firmware, and/or software implementations of aspects of systems. The use of hardware, firmware, and/or software can therefore generally represent (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle can vary with the context in which the processes and/or systems and/or other technologies are deployed. For example, if an implementer determines that speed and accuracy are paramount, the implementer and/or designer of the camouflage positional element(s) and/or the camouflage may opt for mainly a hardware and/or firmware vehicle. In alternate embodiments, if flexibility is paramount, the implementer and/or designer may opt for mainly a software implementation. In yet other embodiments, the implementer and/or designer may opt for some combination of hardware, software, and/or firmware. Hence, there are several possible techniques by which the processes and/or devices and/or other technologies described herein may be effected, none of which is inherently superior to the other in that any vehicle to be utilized is a choice dependent upon the context in which the vehicle can be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

All of the above U.S. patents, U.S. patent application publications, U.S. patent applications, foreign patents, foreign patent applications and non-patent publications referred to in this specification and/or listed in any Application Data Sheet, are incorporated herein by reference, in their entireties.

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", "operably linked", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

It is to be understood by those skilled in the art that, in general, that the terms used in the disclosure, including the drawings and the appended claims (and especially as used in the bodies of the appended claims), are generally intended as "open" terms. For example, the term "including" should be interpreted as "including but not limited to"; the term "having" should be interpreted as "having at least"; and the term "includes" should be interpreted as "includes, but is not limited to"; etc. In this disclosure and the appended claims, the terms "a", "the", and "at least one" positioned prior to one or more goods, items, and/or services are intended to apply inclusively to either one or a plurality of those goods, items, and/or services.

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that could have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that could have A alone, B alone, C alone, A and B together, A and C together, B and C together, and/or A, B, and C together, etc.).

Those skilled in the art will appreciate that the herein-described specific exemplary processes and/or devices and/or technologies are representative of more general processes and/or devices and/or technologies taught elsewhere herein, such as in the claims filed herewith and/or elsewhere in the present application.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. An electrode positioning defibrillator apparatus, comprising:
    a defibrillator apparatus including
        a housing having wheels physically coupled onto exterior opposing surfaces, the housing enclosing
            a capacitor operably coupled to a first and a second defibrillation electrode,
            a battery for charging the capacitor sufficiently to establish a defibrillating charge, and
            a processor configured to control delivery of the defibrillating charge to an individual;
    an individual mover component including a wedge-shaped surface attached to a distal end of the housing with the first defibrillation electrode integrated onto an inclined surface of the wedge-shaped surface; and
    a linkage having a proximal and distal end with the distal end coupled to the second defibrillation electrode and the proximal end coupled to a top surface of the housing, the linkage electromechanically moveable relative to the housing between at least a first position and a second position.

2. The electrode positioning defibrillator apparatus of claim 1, wherein the linkage is configured to electromechanically extend, retract, or telescope between the at least first position and the second position.

3. The electrode positioning defibrillator apparatus of claim 1, wherein the linkage is configured to electromechanically telescope between the at least first position and the second position.

4. The electrode positioning defibrillator apparatus of claim 1, wherein the linkage is extendable or retractable between the at least first position and the second position.

5. The electrode positioning defibrillator apparatus of claim 1, wherein the linkage is configured to extend, retract, or telescope, via a telescoping member, between the at least first position and the second position.

6. The electrode positioning defibrillator apparatus of claim 1, wherein the wedge-shaped surface is sized to reposition the individual by rolling over the individual.

* * * * *